United States Patent
Medema et al.

(10) Patent No.: US 11,103,350 B2
(45) Date of Patent: Aug. 31, 2021

(54) PULL-THROUGH CHORDAE TENDINEAE SYSTEM

(71) Applicant: On-X Life Technologies, Inc., Austin, TX (US)

(72) Inventors: Ryan Medema, Plugerville, TX (US); Daniel Tomko, Dallas, GA (US); Jeffery Poehlmann, Austin, TX (US); Michael Hunt, Austin, TX (US); Kellen Moulton, Austin, TX (US)

(73) Assignee: ON-X LIFE TECHNOLOGIES, INC., Austin, TX (US)

( * ) Notice: Subject to any disclaimer, the term of this patent is extended or adjusted under 35 U.S.C. 154(b) by 199 days.

(21) Appl. No.: 16/305,945

(22) PCT Filed: Jun. 1, 2017

(86) PCT No.: PCT/US2017/035463
§ 371 (c)(1),
(2) Date: Nov. 30, 2018

(87) PCT Pub. No.: WO2017/210434
PCT Pub. Date: Dec. 7, 2017

(65) Prior Publication Data
US 2019/0117400 A1 Apr. 25, 2019

Related U.S. Application Data

(60) Provisional application No. 62/447,681, filed on Jan. 18, 2017, provisional application No. 62/343,957, filed on Jun. 1, 2016.

(51) Int. Cl.
*A61F 2/24* (2006.01)
*A61B 17/04* (2006.01)
*A61B 17/00* (2006.01)

(52) U.S. Cl.
CPC ........ *A61F 2/2457* (2013.01); *A61B 17/0401* (2013.01); *A61B 2017/00243* (2013.01);
(Continued)

(58) Field of Classification Search
CPC ........ A61B 17/0401; A61B 2017/0406; A61B 2017/0417; A61B 2017/0464; A61F 2/2457
See application file for complete search history.

(56) References Cited

U.S. PATENT DOCUMENTS 5,307,924 A 5/1994 Manosalva
5,391,182 A 2/1995 Chin
(Continued)

FOREIGN PATENT DOCUMENTS

AU 2015200387 A1 2/2015
CA 2369641 C 2/2009
(Continued)

OTHER PUBLICATIONS

Wikipedia, "Treasury Tag," http://en.wikipedia.org/wiki/Treasury_tag, Oct. 28, 2014, two pages.
(Continued)

*Primary Examiner* — Wade Miles
(74) *Attorney, Agent, or Firm* — Trop, Pruner & Hu, P.C.

(57) ABSTRACT

An embodiment includes an artificial chordae tendineae system comprising: a first needle; a flexible first chord coupled to a proximal end portion of the first needle; a first proximal pledget coupled to a proximal end portion of the first chord; a first distal conduit coupled to the first chord between the first proximal pledget and the first needle; wherein: the first distal conduit includes first and second faces; one of the first and second faces includes a first aperture; a sidewall of the first conduit, located between the first and second faces, includes a sidewall aperture that does
(Continued)

not directly connect to the first aperture; the sidewall aperture is configured to include a portion of the first chord when the first distal conduit is permanently implanted adjacent tissue but not when the first distal conduit is traversing the tissue before being permanently implanted adjacent the tissue.

13 Claims, 13 Drawing Sheets

(52) U.S. Cl.
CPC ............... A61B 2017/0406 (2013.01); A61B 2017/0409 (2013.01); A61B 2017/0417 (2013.01); A61B 2017/0419 (2013.01); A61B 2017/0464 (2013.01); A61F 2210/0014 (2013.01); A61F 2220/0075 (2013.01)

(56) References Cited

U.S. PATENT DOCUMENTS

| | | |
|---|---|---|
| 5,431,666 A | 7/1995 | Sauer |
| 6,010,531 A | 1/2000 | Donlon |
| 6,797,002 B2 | 9/2004 | Spence |
| 6,869,444 B2 | 3/2005 | Gabbay |
| 6,945,996 B2 | 9/2005 | Sedransk |
| 6,966,916 B2 | 11/2005 | Kumar |
| 6,997,950 B2 | 2/2006 | Chawla |
| 7,241,257 B1 | 7/2007 | Ainsworth |
| 7,635,386 B1 | 12/2009 | Gammie |
| 7,645,286 B2 | 1/2010 | Catanese |
| 7,758,594 B2 | 7/2010 | Lamson |
| 7,766,923 B2 | 8/2010 | Catanese |
| 7,871,368 B2 | 1/2011 | Zollinger |
| 7,871,433 B2 | 1/2011 | Lattouf |
| 7,905,889 B2 | 3/2011 | Catanese |
| 7,951,158 B2 | 5/2011 | Catanese |
| 8,007,503 B2 | 8/2011 | Catanese |
| 8,157,719 B1 | 4/2012 | Ainsworth |
| 8,157,815 B2 | 4/2012 | Catanese |
| 8,216,254 B2 | 7/2012 | Lamson |
| 8,292,884 B2 | 10/2012 | Levine |
| 8,303,622 B2 | 11/2012 | Alkhatib |
| 8,323,336 B2 | 12/2012 | Hill |
| 8,333,776 B2 | 12/2012 | McLean |
| 8,343,187 B2 | 1/2013 | Cheng |
| 8,394,110 B2 | 3/2013 | Catanese |
| 8,425,535 B2 | 4/2013 | McLean |
| 8,439,969 B2 | 5/2013 | Gillinov |
| 8,500,800 B2 | 8/2013 | Maisano |
| 8,545,551 B2 | 10/2013 | Loulmet |
| 8,545,553 B2 | 10/2013 | Zipory |
| 8,663,243 B2 | 3/2014 | Lamson |
| 8,715,239 B2 | 5/2014 | Lamson |
| 8,715,298 B2 | 5/2014 | Catanese |
| 8,758,393 B2 | 6/2014 | Zentgraf |
| 8,778,016 B2 | 7/2014 | Janovsky |
| 8,900,252 B2 | 12/2014 | Lamson |
| 8,936,609 B2 | 1/2015 | Catanese |
| 8,939,996 B2 | 1/2015 | Cheng |
| 9,060,858 B2 | 6/2015 | Thornton |
| 9,320,511 B2 | 4/2016 | McLean |
| 9,480,565 B2 | 11/2016 | Medema |
| 9,549,739 B2 | 1/2017 | Catanese |
| 10,105,132 B2 | 10/2018 | Lamson |
| 2002/0019649 A1 | 1/2002 | Sikora |
| 2002/0068849 A1 | 6/2002 | Schweich |
| 2002/0188170 A1 | 12/2002 | Santamore |
| 2003/0105519 A1 | 6/2003 | Fasol |
| 2004/0073301 A1 | 4/2004 | Donlon |
| 2004/0093023 A1 | 5/2004 | Allen |
| 2005/0038509 A1 | 2/2005 | Ashe |
| 2005/0277966 A1 | 12/2005 | Ewers |
| 2005/0277981 A1 | 12/2005 | Maahs |
| 2006/0030885 A1 | 2/2006 | Hyde |
| 2006/0287716 A1 | 12/2006 | Banbury |
| 2007/0049952 A1 | 3/2007 | Weiss |
| 2007/0051377 A1 | 3/2007 | Douk |
| 2007/0073316 A1 | 3/2007 | Sgro |
| 2007/0100375 A1 | 5/2007 | Mikkaichi |
| 2007/0112338 A1 | 5/2007 | Cohen |
| 2007/0112385 A1 | 5/2007 | Conlon |
| 2007/0118151 A1 | 5/2007 | Davidson |
| 2007/0118213 A1 | 5/2007 | Loulmet |
| 2008/0195126 A1 | 8/2008 | Solem |
| 2008/0208219 A1 | 8/2008 | Suzuki |
| 2008/0228223 A1 | 9/2008 | Alkhatib |
| 2008/0228272 A1 | 9/2008 | Moaddeb |
| 2009/0043381 A1 | 2/2009 | Macoviak |
| 2009/0088837 A1 | 4/2009 | Gillinov |
| 2009/0177274 A1 | 7/2009 | Scorsin |
| 2009/0182192 A1 | 7/2009 | Shiono |
| 2010/0023118 A1 | 1/2010 | Medlock |
| 2010/0042147 A1 | 2/2010 | Janovsky |
| 2010/0179574 A1 | 7/2010 | Longoria |
| 2010/0249919 A1 | 9/2010 | Gillinov |
| 2011/0011917 A1 | 1/2011 | Loulmet |
| 2011/0060407 A1 | 3/2011 | Ketai |
| 2012/0209377 A1 | 8/2012 | Machold |
| 2013/0006352 A1 | 1/2013 | Yaron |
| 2013/0096673 A1 | 4/2013 | Hill |
| 2013/0110230 A1 | 5/2013 | Solem |
| 2013/0204079 A1* | 8/2013 | Catanese, III ......... A61B 17/10 600/37 |
| 2013/0282059 A1 | 10/2013 | Ketai |
| 2014/0114404 A1 | 4/2014 | Gammie |
| 2014/0142689 A1 | 5/2014 | DeCanniere |
| 2014/0364938 A1 | 12/2014 | Longoria |
| 2015/0045879 A1* | 2/2015 | Longoria ............... A61B 17/06 623/2.12 |
| 2015/0216662 A1 | 8/2015 | Medema |
| 2016/0220372 A1 | 8/2016 | Medema |
| 2017/0105838 A1 | 4/2017 | Medema |

FOREIGN PATENT DOCUMENTS

| | | |
|---|---|---|
| EP | 2023822 A2 | 2/2009 |
| EP | 2741711 A2 | 6/2014 |
| WO | 2012040865 A1 | 4/2012 |
| WO | 2012137208 A1 | 10/2012 |
| WO | 2014028725 A1 | 2/2014 |
| WO | 2014093861 A1 | 6/2014 |

OTHER PUBLICATIONS

Uline, "Long Needle Price Tag Gun / Fasteners," Online Catalog, http://www.uline.com/BL_476/Long-Needle-Price-Tag-Gun-Fasteners, Jan. 23, 2015, one page.
Hongyu Plastic String Co., Limited, "Elastic Rope With Metal Tipping/Elastic Treasury Tag," Online Catalog, http://hysjsd.en.alibaba.com/productlist.html, Jan. 30, 2015, four pages.
Kendall, "Fixation Device ProTack Pistol Grip 30 Titanium Helical Fasteners," Supreme Med, Mnf #: 174006, http://www.suprememed.com/fixation-device-protack-pistol-grip-30-titanium-helicalfasteners-152138, Feb. 1, 2016, one page.
"Ti-Knot® Device: Features," LSI Solutions®, Isisolutions.com, Dec. 23, 2009, https://web.archive.org/web/20091223024458/http://www.lsisolutions.com/tkfeatures, two pages.
Seeburger, et al., "Trans-apical beating-heart implantation of neochordae to mitral valve leaflets: results of an acute animal study," European Journal of Cardio-Thoracic Surgery 41.1 (2012), four pages.
Farndons Limited, "Solutions," Catalog, http://www.farndons.com/flipbook/Farndons-Catalogue-2015/files/assets/common/downloads/Farndons-Retail-Catalogue-2012.pdf,. Feb. 1, 2016, seven pages.
smallbusinesssupplies.net, "Products: Standard Tag-It 2 Barbs," Small Business Supplies, http://www.smallbusinesssupplies.net/tagging-guns-supplies.
Salvador, et al., "A 20-year experience with mitral valve repair with artificial chordae in 608 patients," The Journal of Thoracic and Cardiovascular Surgery 135.6 (2008), nine pages.

(56) References Cited

OTHER PUBLICATIONS

Bajona, et al., "Beating-heart, off-pump mitral valve repair by implantation of artificial chordae tendineae: an acute in vivo animal study," The Journal of thoracic and cardiovascular surgery 137.1 (2009), five pages.

Bajona, et al., "Tension measurement of artificial chordae tendinae implanted between the anterior mitral valve leaflet and the left ventricular apex: an in vitro study," Innovations: Technology and Techniques in Cardiothoracic and Vascular Surgery 3.1 (2008), five pages.

Ionescu, et al., "Autologous fascia lata for heart valve replacement," Thorax 25.1 (1970), 11 pages.

Ionescu, et al., "Mitral valve replacement with aortic heterografts in humans," Thorax 22.4 (1967), ten pages.

Chiappini, et al., "Replacement of chordae tendineae with polytetrafluoroethylene (PTFE) sutures in mitral valve repair: early and long-term results," Journal of Heart Valve Disease 15.5 (2006), seven pages.

Today's Homeowner With Danny Lipford "Testing Wall Anchors and Picture Hangers," https://www.todayshomeowner.com/testing-wall-anchors-and-picture-hangers/, 2008, eight pages.

International Searching Authority, Notification of Transmittal of the International Search Report and the Written Opinion of the International Searching Authority dated May 16, 2016 in International Application No. PCT/US2016/016156, 12 pages.

International Searching Authority, Written Opinion of the International Searching Authority and the International Search Report dated Sep. 8, 2017 in International Application No. PCT/US2017/035463, nine pages.

\* cited by examiner

PULL-THROUGH CHORDAE TENDINEAE SYSTEM

PRIORITY CLAIM

This application claims priority to: (a) U.S. Provisional Patent Application No. 62/343,957, filed on Jun. 1, 2016 and entitled "Pull-Through Chordae Tendineae System (for mitral chordae tendineae repair/replacement)", and (b) U.S. Provisional Patent Application No. 62/447,681, filed on Jan. 18, 2017 and entitled "Pull-Through Chordae Tendineae System (for mitral chordae tendineae repair/replacement)". The content of each of the above applications is hereby incorporated by reference.

TECHNICAL FIELD

Embodiments of the invention are in the field of cardiology-related medical devices.

BACKGROUND

Mitral valve prolapse is a significant cause of cardiovascular morbidity and mortality. As a result, surgical intervention is often required. As one of the surgical options currently available, mitral valve repair is well established and is applicable in patients with mitral valve prolapse due to degenerative mitral valve disease. The techniques of mitral valve repair include inserting a cloth-covered ring around the valve to bring the leaflets into contact with each other (annuloplasty), removal of redundant/loose segments of the leaflets (quadrangular resection), and re-suspension of the leaflets with artificial chordae (chordal replacement).

BRIEF DESCRIPTION OF THE DRAWINGS

Features and advantages of embodiments of the present invention will become apparent from the appended claims, the following detailed description of one or more example embodiments, and the corresponding figures. Where considered appropriate, reference labels have been repeated among the figures to indicate corresponding or analogous elements.

DETAILED DESCRIPTION

Figure 1:
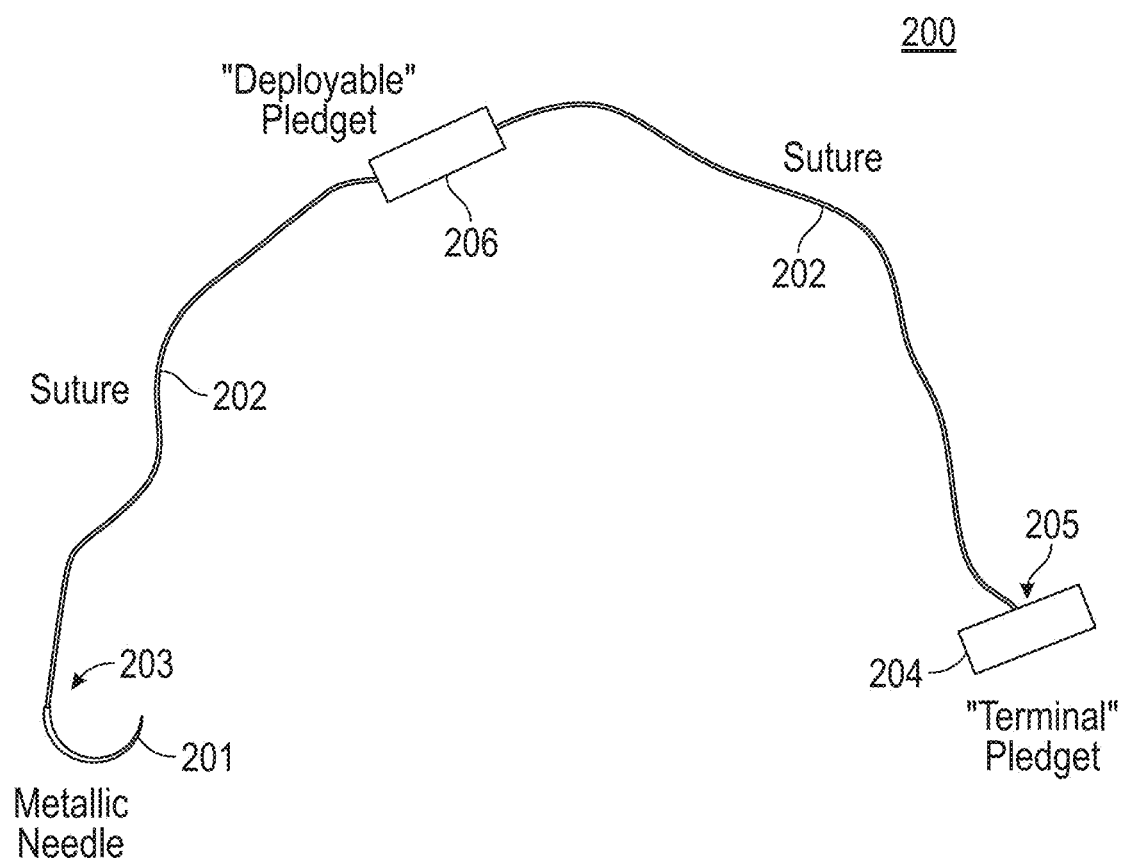
FIG. 1 includes an embodiment with a needle and two pledgets.

Reference will now be made to the drawings wherein like structures may be provided with like suffix reference designations. In order to show the structures of various embodiments more clearly, the drawings included herein are diagrammatic representations of structures. Thus, the actual appearance of the fabricated structures, for example in a photograph, may appear different while still incorporating the claimed structures of the illustrated embodiments. Moreover, the drawings may only show the structures useful to understand the illustrated embodiments. Additional structures known in the art may not have been included to maintain the clarity of the drawings. "An embodiment", "various embodiments", and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical contact with each other and "coupled" may indicate elements co-operate or interact with each other, but they may or may not be in direct physical contact.

Regarding chordal replacement addressed above, replacement of diseased mitral valve chordae with expanded polytetrafluoroethylene (ePTFE) sutures is an established technique with good long-term results. Various techniques have been described to assist the surgeon to establish the correct replacement chordal length. However, despite the surgical challenges of attaching the ePTFE suture to papillary muscles and determining the correct length for artificial chordae, few effective products have been developed to assist surgeons with this challenging procedure. In general, surgical approaches have centered on individual surgeon-based techniques including the use of a small tourniquet or weaving the suture through the leaflet to the mitral annulus and thereafter readjusting the length while the ventricle is filled under pressure. Other conventional techniques and products require the surgeon to take a large role in the surgery. For example, the surgeon must fabricate desired lengths of suture and then position, install, and adjust the suture lengths and finally tie a series of knots to secure the prosthesis. Applicant has noted how these varying techniques lead to inconsistencies and varying levels of clinical success.

Embodiments address various problems found in conventional systems. An embodiment is a rapid deployment system that requires significantly less of the surgeon and dramatically shortens the duration of the surgery. An embodiment includes a prosthesis system that allows a surgeon to quickly implant a prefabricated artificial chordae tendineae prosthesis (e.g., to repair mitral valve regurgitation or prolapse). The embodiment allows the surgeon to fully deploy the implant, completely or almost completely eliminating the need for the surgeon to tie complicated and time-consuming knot bundles, or crimp additional components to secure the prosthesis (as is the case with conventional crimping systems). Embodiments allow the surgeon to pull a strand or strands of ePTFE suture and a series of pledgets through cardiac tissues to install the implant, completely eliminating the need for the surgeon to tie complicated and time-consuming knot bundles, or crimp additional components to secure the prosthesis. Finally, embodiments allow for minimally invasive (e.g., through a space between a patient's ribs) and trans-catheter deployment of the prosthesis, ultimately enabling quicker procedures and better patient outcomes.

Embodiments of the invention addressed herein include various apparatuses, systems, and surgical techniques.

FIG. 1 includes an embodiment. The overall concept of an embodiment of the prosthesis is a length of suture (e.g., monofilament or braided), coupled with a needle (e.g., metallic needle) and at least two pledgets—a "terminal" pledget and one (or more) "deployable" pledgets. In an embodiment the distance between the deployable and terminal pledgets is a pre-determined and fixed length, and generally becomes or corresponds with the effective length of the artificial chord. This is a pre-configured construct, delivered to the surgeon sterile and ready to use. No additional supplies or materials are necessary.

FIGS. 18(A)-18(F) depict varying chordae structures in embodiments of the invention. For each of these figures a length of suture or chord that terminates with a needle is not shown. For example, the figures are analogous to the portion of FIG. 1 extending from the terminal pledget to the deployable pledget but do not include the portion of FIG. 1 extending from the deployable pledget to the needle. FIGS. 18(G)-18(H) depict the embodiment of FIG. 18(E) during different stages of its deployment.

Figure 18A:
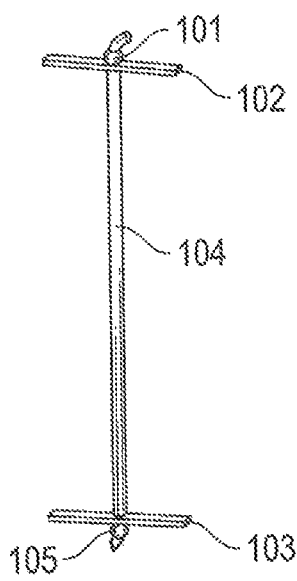
FIGS. 18(A)-18(F) depict varying chordae structures in embodiments of the invention. In these figures a suture length affixed to a needle has already been separated from the remaining pledgets.
Figure 18B:
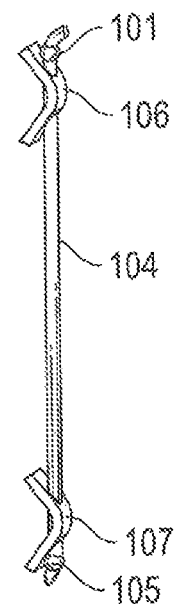
Figure 18C:
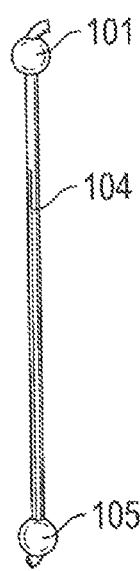
Figure 18D:
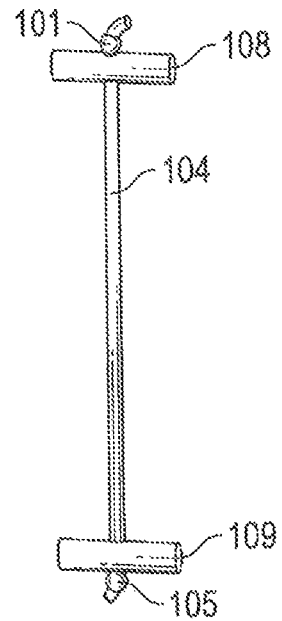

FIG. 18(A) includes mechanical knots or melted ePTFE sutures 101, 105, PTFE strips 102, 103, and ePTFE suture 104. FIG. 18(B) includes components similar to FIG. 18(A) but further adds PTFE felt pledgets 106, 107 in place of the PTFE strips of FIG. 18(A). FIG. 18(F) is similar to FIG. 18(B) but includes pledgets shaped differently from those of FIG. 18(B). FIG. 18(C) is similar to FIG. 18(A) but foregoes PTFE strips or pledgets and instead relies on knots 101, 105 being enlarged and configured to compress (e.g., when passing through tissue or a catheter) but then expand to offer secure purchase to leaflet or papillary tissue. FIG. 18(D) includes components similar to FIG. 18(A) but further adds thickened ePTFE suture portions 108, 109 in place of the PTFE strips of FIG. 18(A).

Figure 18E:
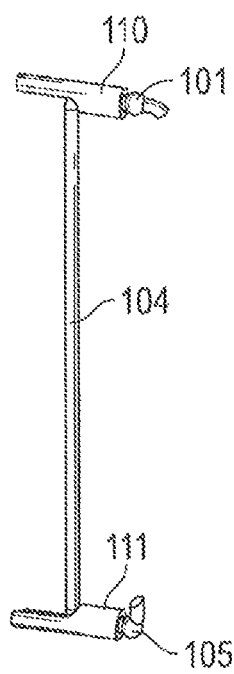
Figure 18F:
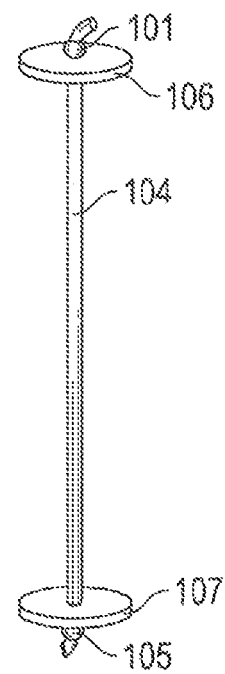
Figure 18G:
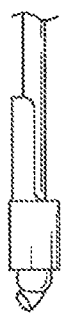
FIGS. 18(G)-18(H) depict the embodiment of FIG. 18(E) during different stages of its deployment.
Figure 18H:
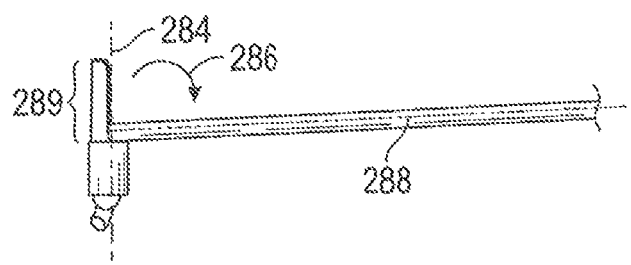

FIG. 18(E) includes components similar to FIG. 18(A) but further adds slotted ePTFE tubes 110, 111 in place of the PTFE strips of FIG. 18(A). The slotted tube embodiment of FIG. 18(E) offers a small cross sectional diameter (when collapsed, such as FIG. 18(G)) while still offering a broad and reliable anchoring feature (once deployed via 90 degree rotation, such as FIG. 18(H)). The slotted tube is sometimes referred to herein as a "fluke" or "ferrule" or some form of conduit (a pipe or tube or trough through which something (such as suture) passes). As used herein, a conduit need not be an overly extended cylinder having that is completely straight or has any particular length. The conduit may include a mere trough that acts to restrain the suture therein.

Embodiments of FIGS. 18(A)-18(F) feature a premeasured length of ePTFE 104 and a method of capping both ends of the construct with PTFE and/or ePTFE components (which may be rigid in some embodiments). ePTFE and PTFE have excellent biocompatibility, resistance to degradation, flexibility, and a long clinical history of use. Each of these assemblies comprises artificial mitral chordae tendineae prosthesis.

Figure 15:
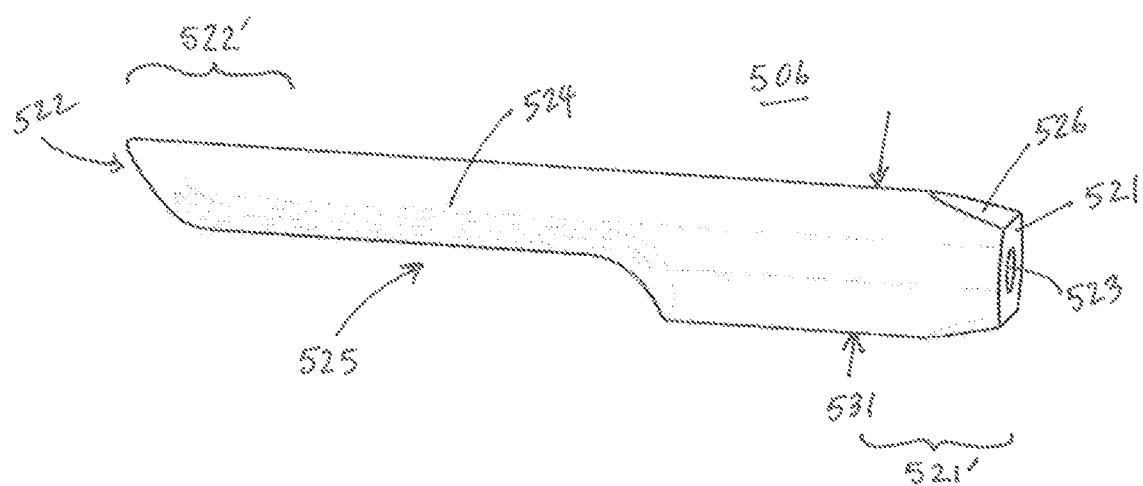
FIG. 15 includes an embodiment of a pledget which includes a conduit or ferrule.

While there are many embodiments for deployable pledgets, many embodiments share a feature—namely they are configured to pass through cardiac tissues easily by design (e.g., may include a "lead in" taper where narrower portion of taper inserts through tissue first, such as FIG. 15), and then expand, rotate, engage, and/or activate, etc. (deploy) such that they will not return through the tissue. Furthermore, once deployed the pledget distributes the chordal force onto a larger area in order to protect the native tissues from damage. Materials for pledgets may include, for example, ePTFE/PTFE tubing, ePTFE/PTFE felt, Silicone, Polypropylene, Shape Memory Polymers, Shape Memory Foam, Nitinol, PCU or PET. Pledgets may be permanent, or may feature biodegradable elements to facilitate their deployment and incorporation into native tissues.

As seen in FIG. 18(E), a single piece of suture may pass through the pledget while in other embodiments two or more sutures are coupled by the pledget. Multiple sutures may couple together via a knot or may be fused together (e.g., via melted or heated ePTFE). In an embodiment the first and second suture lengths may include separate ePTFE strands joined together via heat (e.g., laser), weld, chemical reaction, and the like.

Embodiments of pledgets may include a variation on the slotted tube of FIG. 18(G). For example, a central slot is located in the fluke such that a knot may nest within the slot to create a streamlined profile. In other words, this allows two or more sutures to be knotted together with the knot not constituting a barrier to passage through tissue. However, the knot may be made in a single piece of suture but used to hold the fluke pledget in place.

In another embodiment of a slotted tube a knot bundle is originally placed in line with tube (for easy tissue penetration). When a suture is cut the suture slides and the knot bundle rests perpendicular at the center of the tube.

Other embodiments of pledgets are similar in form and function to a molly bolt, having a slim profile that deforms resulting in a wider cross section.

Another embodiment of a pledget is similar to an umbrella, including struts with fabric that are retracted when passing through tissue and then deploy to create a wide cross section.

Another embodiment of a pledget includes a coil of wire (e.g., shape memory alloy) or polymer (shape memory polymer) that straightens out during deployment but then, based on heat or some other activity, resumes its programmed shape (e.g., coil) that resists passage through tissue.

FIGS. 18(A)-18(H) show not only many embodiments for deployable pledgets, such as pledgets 102, 106, 108, 110, those figures also show many embodiments for terminal pledgets, such as pledgets 103, 107, 109, 111. A common feature among many embodiments of terminal pledgets, such as the embodiment of FIG. 12 (which will be addressed below), is that they will not pass through cardiac tissues and instead act as a terminal connection to anchor the construct. Furthermore, the terminal pledget distributes the chordal force onto a larger area in order to protect the native tissues from damage. Some embodiments are single chordal member designs while others use purposeful routing of the suture to form a continuous construct offering multiple chordal members.

An embodiment of a terminal pledget includes a relatively larger flexible "button" (made of, for example, silicone) over molded or cast onto the suture tail, to distribute load and eliminate stress concentrations.

An embodiment for terminal pledgets includes a method for joining multiple strands into a single pledget. Multiple strands may be used for many embodiments.

An embodiment for a terminal pledget includes a saucer shape over molded/cast onto suture tails. Doing so distributes load while allowing the tip of the saucer to be flexible.

Materials for terminal pledgets include, for example, ePTFE/PTFE tubing, ePTFE/PTFE felt, Silicone, Polypropylene, Shape Memory Polymers, Shape Memory Foam, Nitinol, PCU, PET, PLA, PGA, PLGA. Pledgets may be permanent, or may feature biodegradable elements to facilitate their incorporation into native tissues.

Figure 8:
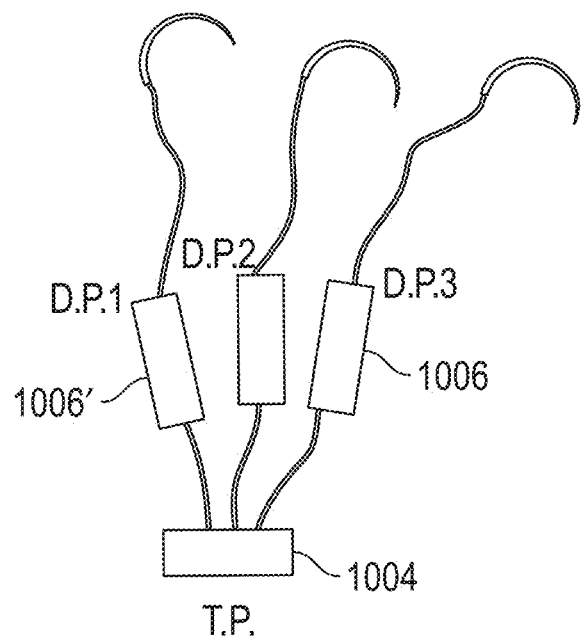
FIG. 8 includes an embodiment with multiple needles and pledgets.

FIG. 8 includes an embodiment that features multiple (two or more) "Deployable Pledgets" configured to a single "Terminal Pledget", which results in multiple chordal members. Embodiments may be achieved with separate independent suture strands, or the purposeful routing of a single strand to fabricate multiple chordal members. For example, instead of the single strands shown in FIG. 8 an alternative embodiment may include loops such that a single suture may start at the terminal pledget, then pass through a first deployable pledget and back through the first deployable pledget back to the terminal pledget (thereby forming a loop). The process may then be repeated with the same suture to attach additional loops to one or more additional pledgets.

Figure 9:
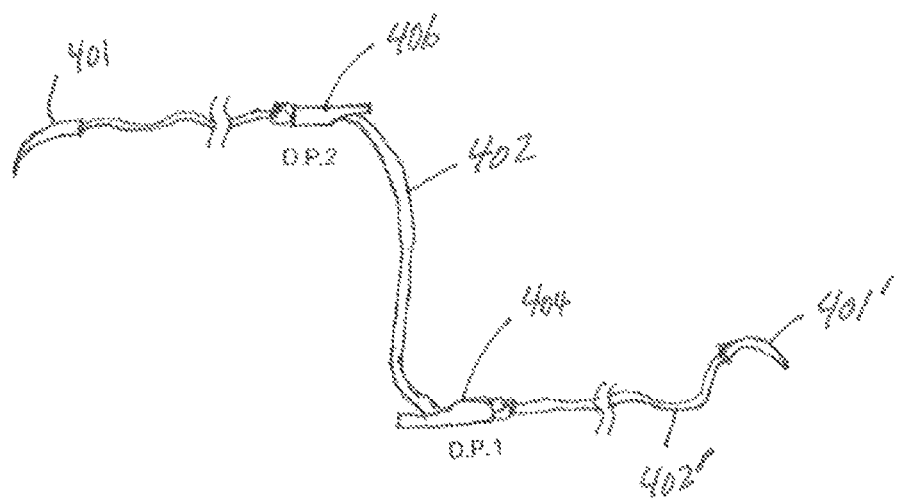
FIG. 9 includes an embodiment with multiple needles and pledgets.
Figure 10:
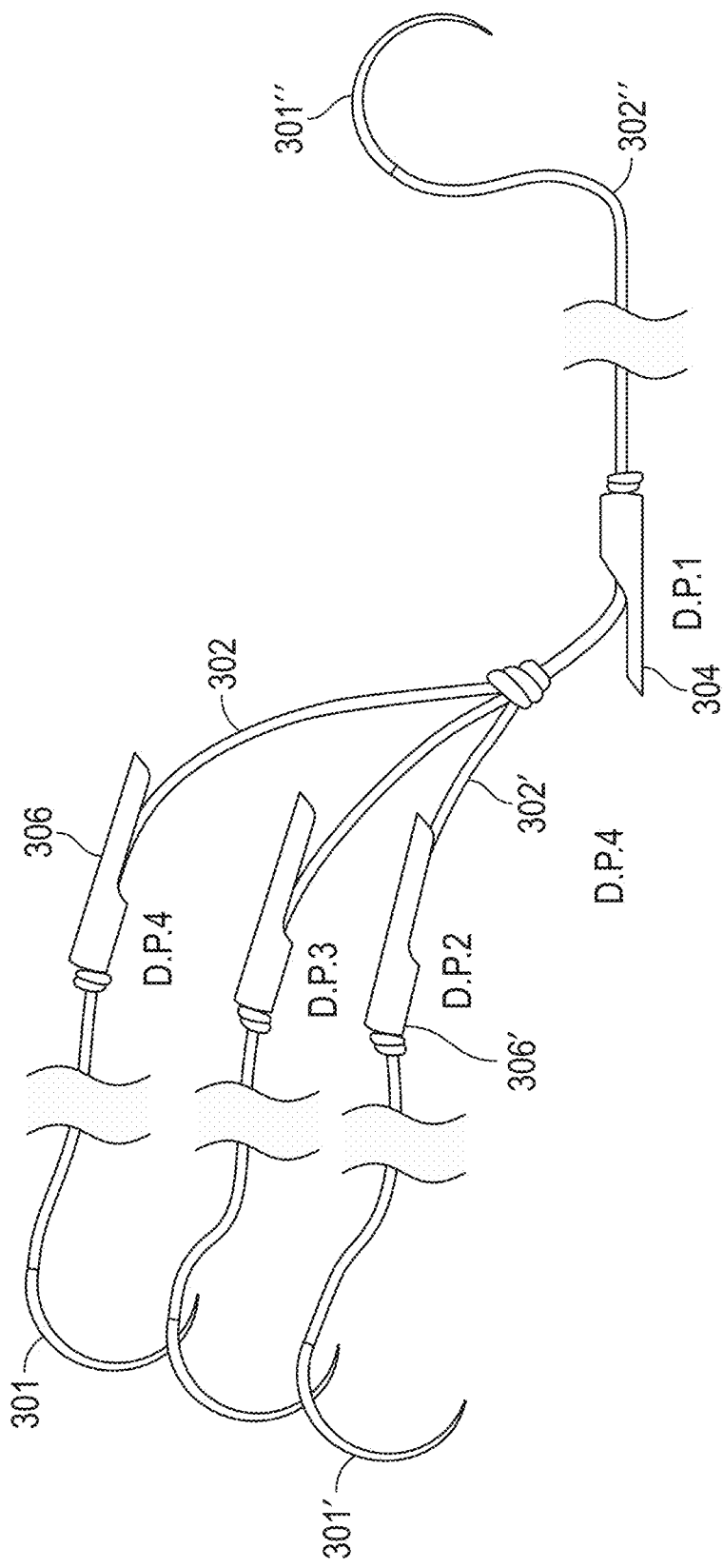
FIG. 10 includes an embodiment with multiple needles and pledgets.

FIG. 9 includes an embodiment that features one "deployable pledget" coupled to another deployable pledget. FIG. 10 includes an embodiment that features one "deployable pledget" coupled to multiple deployable pledgets. Needles (e.g., metallic needles) are coupled to each end of the suture segment(s) facilitating penetration through the cardiac tissues. The single and multiple chord member embodiments of FIGS. 9-10 both provide that when an embodiment is installed between a leaflet and papillary muscle each pledget passes through only one tissue (rather than previous embodiments where some pledgets must pass through both tissues). For example, element 306 of FIG. 9 deploys through a leaflet and element 304 deploys through papillary muscle.

Unlike other embodiments addressed herein that include a pledget at the leaflet (whether terminal or deployable), other embodiments minimize bulk above the leaflet and instead maintain a flat and smooth coaptation zone on the repaired leaflet. For example, the suture may be passed through the papillary muscle, then the leaflet, then the leaflet again, and then through the papillary muscle. This provides a "clean leaflet". As a result, two pledgets may be adjacent the papillary muscle but not adjacent the leaflet. These pledgets may be T-bars (another word for conduit of FIG. 15)/flukes that have rotated 90 degrees after passage through the papillary muscle. Other embodiments provide placing the leaflet pledget on the underside of the leaflet (FIGS. 13-14), rather than on top of the leaflet. This provides a "pledget beneath leaflet" configuration.

An embodiment eliminates the need for surgeon-tied knots and crimping to execute artificial mitral chordae tendineae. Also, such an embodiment requires no delivery device and limited external supplies to implement. Simply put, in an embodiment the clinician penetrates native cardiac tissues and then pulls the device through the tissue until termination, finally trimming off the unused portion. Previously, the surgeon had many steps and required a great deal of skill and operating room time to fabricate and implant artificial chordae tendinae devices, complete with many manual knots.

An embodiment includes a sealed kit (e.g., package) including a first suture portion coupled between first and second pledgets and a second suture portion coupled between the second pledget and a needle. (e.g., FIG. 9 or 10) In an embodiment the first and second suture portions are monolithic with each other but not so in other embodiments. In an embodiment one of the first and second pledgets is configured to pass through tissue with limited resistance and the other of the first and second pledgets is configured to resist passage through tissue with limited resistance. In an embodiment one of the first and second pledgets comprises a fluke that in a first configuration has a long axis generally collinear with a long axis of one of the first and second suture portions and in a second configuration has a long axis generally orthogonal or at least non-collinear with a long axis of one of the first and second suture portions.

An embodiment includes a kit that includes multiple chords in a variety of predetermined lengths, which will allow the surgeon to accurately achieve the correct geometry for that particular patient. This feature eliminates or reduces the variability that comes from a hand-tied prosthesis, and ultimately offers a more consistent product. In a related method, the surgeon may elect to place several prostheses about a single leaflet or multiple leaflets. In such a case the surgeon may simply repeat the process in, for example, FIG. 1 to implant more than one chord. The papillary muscle and leaflet are such that they can handle several "pokes" or penetrations by delivery needles to implant chordae, considering the relatively small diameter of the delivery needles. As a result, the surgeon has an "in-and-out technique" that capitalizes on simplicity and quickness and the ability to deploy 1 or more chordae. For example, three different "shots" or penetrations with delivery needles (to deploy 3 chordae) (e.g., FIG. 12) would be tolerable by papillary muscle and a leaflet.

In an embodiment the prosthesis that is implanted is comprised entirely of ePTFE and/or PTFE, which allows for excellent biocompatibility and tissue ingrowth into the construct. However, other embodiments use other materials for the chord (e.g., nylon) and the fluke of the prosthesis may be fabricated from a polymer or metal (e.g., Nitinol) that allows the fluke to collapse about the chord. Thus, for embodiments described herein as including ePTFE different versions of those same embodiments may include PTFE or other similar materials.

Furthermore, embodiments may provide materials with doping. For example, the ePTFE and/or PTFE materials described immediately above may be doped with any radiopaque material such as bismuth, barium, tungsten, gold, platinum, etc. The doping agent makes the implant ends radiopaque such that the surgeon can monitor the position of the implant during or after surgery.

Regarding the surgical procedure, the orientation of the papillary muscle depends on the individual. Sometimes the muscle is in the base of the heart wall and rises up vertically like a water tower, on others it is on the side of the ventricle and juts out more horizontally. The surgeon may grab the tip of the muscle with forceps and manipulate the muscle to get the preferred orientation for surgery.

In an embodiment the system is a single use disposable attachment device containing a single prosthesis preloaded into the device. The system is delivered to the surgeon sterile.

An embodiment translates to a minimally invasive procedure (e.g., trans-catheter approach or through an intercostal space via transthoracic entry). Since conventional systems require additional instrumentation or surgeon intervention to secure the prosthesis, the conventional systems may have difficulty translating to minimally invasive or trans-catheter deployment. Conventional systems require an open approach and several instruments and components. In contrast, with an embodiment the surgeon inserts one or more sutures lengths into the patient's tissue to deploy the prosthesis and the surgery is complete.

Embodiments may include no knot but instead couple the chords to each other with a weld, or the chords may be monolithic with each other where the coupling is just a location where the cords couple to each other. For example, the chords may be cut or otherwise formed from a single piece of ePTFE.

Various embodiments have been described in conjunction with mitral valve repair but other uses are possible such as tricuspid valve repair or even suturing in locations apart from the heart. For example, there are orthopedic applications such as suturing connective tissue to bone or two soft tissues together in a rapid manner (e.g., coupling tendon to muscle). Specifically, a surgeon may anchor a loose ligament or tendon using an embodiment of the system. One end of the system is secured to the free end of the ligament, while the other is anchored in the bone. In such a case the system may constitute a general anchoring or connective prosthesis.

A pledget is to be interpreted as a buttress or shield to prevent, for example, a suture/coupling member from cutting tissue over time due to repetitive movement or tension of the suture/coupling member. Some embodiments allow for a system to be shipped with no pledget but coupled to a pledget at a later time once the shipping container is opened and is ready for use by the surgeon.

In addition, materials are not restricted to ePTFE and/or PTFE and may include, for example (for the chords and/or flukes) silk, nylon, biodegradable materials (e.g., for suturing that is temporary in nature such as is the case with some orthopedic procedures) such as polyglycolic Acid (PGA), polylactic acid (PLA), poly(lactic-co-glycolic acid) (PLGA), polydioxanone (PDS), poly(orthoester) (POE), polycaprolactone (PCL), polymethylmethacrylate (PMMA), copolymer blends of the above, and the like. Other embodiments may include biological tissue for chord lengths. Also, the system need not be limited to just one material. For example, in the embodiments of FIG. 1 the chords may be PTFE and the flukes may be ePTFE.

As used herein, a "fluke" includes objects like conduits or ferrules that pass the chord there through but then anchor the chord by preventing an end of the chord from passing through the fluke. A fluke, as used herein, is similar to a "treasury tag" or India tag used to fasten sheets of paper together or to a folder. Such a tag includes lace/chord with a tag (e.g., metal or ePTFE) at each end (where the ends are sharpened in some embodiments). The tags may be threaded through apertures in documents, tissue, and the like. The tag may be orthogonal to the lace upon deployment but in line with the lace while traversing an aperture. The tag may have a slot or aperture on one half of the cylinder that comprises the tag such that the lace may move from in-line with the tag to orthogonal to the tag (see FIG. 18(E)). The lace/chord may or may not be resilient.

Embodiments described herein reduce variability over current methods. A current method of hand tying artificial chordae prosthetics out of ePTFE suture requires skill on the part of the surgeon. Each knot is comprised of between eight to ten throws in ePTFE suture. The knots could be tied incorrectly or the surgeon could miscount the requisite number of throws resulting in an inferior knot. By eliminating the knot tying altogether, an embodiment eliminates the variability that can be observed in the current method of hand tying artificial chordae prosthetics.

An embodiment reduces operating room (OR) time compared to current methods. Since the prosthetic is not fabricated during surgery, the duration that the patient is in surgery is reduced.

In an embodiment a staple or cinch may be coupled to the chord ends. Thus, instead of (or in addition to) heating the chord ends to couple the chords together a cinch/staple/crimped polymeric or metal sleeve may be attached to the distal chord ends.

Note an embodiment is suitable for a trans-catheter approach. For example, a needle (such as needle 201 of FIG. 1) may be advanced via transcutaneous catheter. The needle may couple to a fluid source, which may deploy a chord (e.g., the cord of FIG. 1) from the needle based on fluid pressure (e.g., from a plunger). Of course, other embodiments are not so limited and may include inserting the needle through a space between the patient's ribs.

Figure 14:
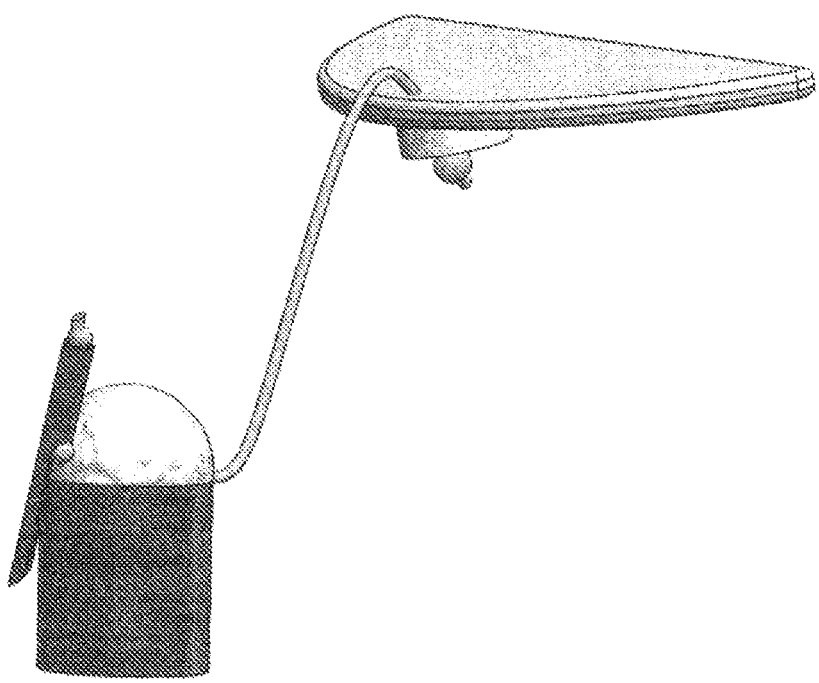

More specifically, the system 200 of FIG. 1 may be delivered transcatheter or via minimally invasive instrumentation through a right mini thoracotomy. In these techniques, the entirety of the prosthesis 200 is housed within the catheter (or MIS instrument), delivered to the left atrium superior to the mitral leaflet, and then deployed through the leaflet tissue and papillary muscle. For example, a stiff rod-like member (which is still flexible enough to be delivered via catheter) may accompany needle 201 through the catheter (or MIS instrument) and drive the needle and deployable pledget through the leaflet and then through papillary muscle. The excess suture and needle would then be cut (using snips or a sharp edge advanced through the catheter/MIS instrument and/or coupled to the rod) and removed (along with the rod used to drive the needle through tissue), thereby leaving behind the finished deployed prosthesis as shown in FIG. 14 (or with the proximal pledget above the leaflet instead of below it as shown in FIG. 14).

Figure 12:
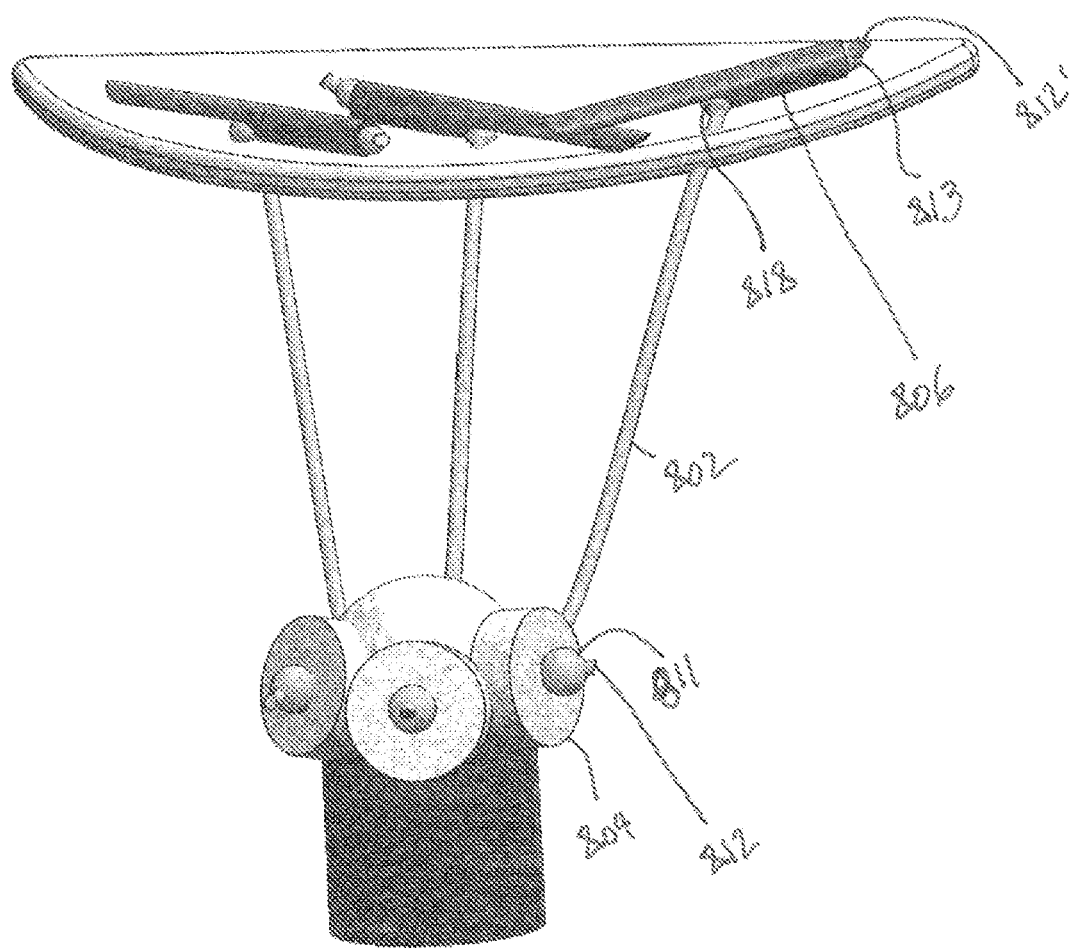
FIG. 12 includes the use of various instances of an embodiment. The chords shown therein may be the same length in some embodiments but different lengths in other embodiments.

FIG. 12 shows a portion of the ferrule between two knots or obstructions to hold the ferrule in place. Also, the portion of the suture including the needle is not always shown in figures presented herein. The needle may have an outer diameter equal to, greater than, or less than the maximum outer diameter of the ferrule (also known as a conduit or T-Bar).

Figure 19A:
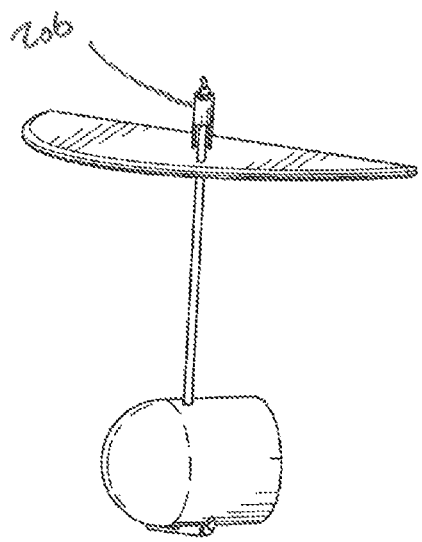
FIGS. 19(A)-19(B) depict the embodiment of FIG. 18(E) during different stages of its deployment. In these figures a suture length affixed to a needle has already been separated from the remaining pledgets.
Figure 19B:
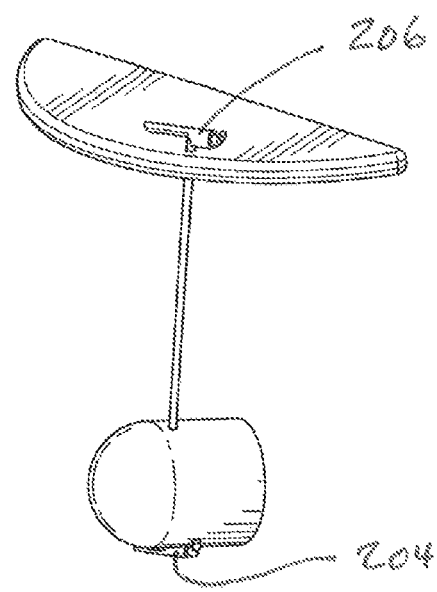

FIG. 1 includes an artificial chordae tendineae system 200 comprising: a first needle 201; a flexible first chord 202 coupled to a proximal end portion 203 of the first needle; a first proximal conduit 204 coupled to a proximal end portion 205 of the first chord; a first distal conduit 206 coupled to the first chord between the first proximal conduit and the first needle. The first chord includes a long axis (see axis 288 of FIG. 18(H)) when the first chord is fully extended into a linear orientation. The first proximal conduit includes a long axis, and the first distal conduit includes a long axis (see axis 284 of FIG. 18(H)). The long axes of the first proximal and distal conduits are substantially parallel to the long axis of the first chord in a first system orientation (see FIG. 18(G) and element 206 of FIG. 19(A)); wherein the first proximal and distal conduits are each configured to rotate (see action 286 of FIG. 18(H) and 204, 206 of FIG. 19(B)) when permanently deployed into a patient in a second system orientation such that the long axes of the first proximal and distal conduits are not parallel (see, e.g., the relationship between axes 284, 288 of FIG. 18(H)) to the long axis of the first chord.

An embodiment may include a kit having two or more of system 200 of FIG. 1. Each system may include a suture having a length between elements 203, 205 that are the same or that are unequal to each other.

FIG. 12 includes a first proximal obstruction 812 between the first proximal conduit (or pledget 804 as shown in FIG. 12) and a proximal end 812 of the first chord 802; and a first distal obstruction 813 between the first distal conduit 806 and the first needle (no longer shown in FIG. 12 after having been severed); a second distal obstruction 818 between the first proximal and distal conduits. Each of the first proximal obstruction 812, the first distal obstruction 813, and the second distal obstruction 818 includes an outer diameter greater than an outer diameter of the first chord 802. The obstructions may simply be knots of suture 802.

In FIG. 1 the first chord 202 is monolithic and passes through the first distal conduit 206. For example, if pledget 206 is a conduit, such as conduit 806 of FIG. 12, chord 802 constitutes a single suture length that extends from end 812 to end 812'. In such a case, the first chord is monolithic and passes through the first proximal 804 and distal 806 conduits. However, in other embodiments the chord may not completely pass through a portion, such as a proximal pledget. In other embodiments the suture may be non-monolithic and coupled together from numerous separate suture lengths.

In FIG. 12 portions of the distal conduit 806 are substantially statically coupled to the first chord 802 so the portions of the first distal conduit 806 do not slide along the first chord by more than 1 mm. This may be due to, for example, obstructions 818, 813.

In an embodiment the first distal conduit (e.g., element 206 of FIG. 1) is deformable. For example, the conduit may include a polyurethane shape memory polymer that expands when warmed by bodily fluids.

In the embodiment of FIG. 1 the first chord 202 includes a first chord material, the first proximal conduit 204 includes a first proximal conduit material, and the first distal conduit 206 includes a first distal conduit material that is the same as the first chord material and the first proximal conduit material (PTFE or ePTFE).

FIG. 10 illustrates proximal conduit 304, first distal conduit 306, suture length 302, first needle 301, second needle 301'; a flexible second chord 302' coupled to a proximal end portion of the second needle, the first proximal conduit 304 being coupled to a proximal end portion of the second chord 302'; a second distal conduit 306' coupled to the second chord between the first proximal conduit and the second needle.

FIG. 10 includes a third needle 301"; a flexible third chord 302" coupled to an end portion of the third needle and to the first proximal conduit 304; wherein the third chord is between the first proximal conduit and the third needle.

FIG. 9 includes proximal conduit 404, first distal conduit 406, suture length 402, first needle 401, second needle 401'; a flexible second chord 402' (which may or may not be monolithic with chord/suture 402) coupled to an end portion of the second needle and to the first proximal conduit 404; wherein the second chord is between the first proximal conduit and the second needle.

FIG. 15 includes first distal conduit 506, which includes first face 521 and second face 522; one of the first and second faces includes a first aperture 523; a sidewall 524 of the first conduit, located between the first and second faces, includes a sidewall aperture 525 that does not directly connect to the first aperture. The sidewall aperture 525 is configured to include a portion of the first chord when the system is in the second system orientation (e.g., FIG. 18(H)) but not when the system is in the first system orientation (e.g., FIG. 18(G)). First distal conduit 506 has a beveled edge 526 to facilitate traversal of the first distal conduit through tissue.

In the embodiment of FIG. 15 and as noted above, the first distal conduit 506 includes first end region 521' and second end region 522' and one of the first and second end regions includes a first aperture 523 through which suture passes. In the case of FIG. 15, it is end portion 521' that includes aperture 523. Accordingly, the end region (region 522' in this case) opposite the end region with aperture 523 (region 521' in this case) does not directly contact a portion of the first chord when the system is in the second system orientation (e.g., FIG. 18(H)—the position taken during permanent implantation) but does directly contact a portion of the first chord when the system is in the first system orientation (e.g., FIG. 18(G)—the position taken during tissue traversal).

Embodiments may include conduits which include a knot or coupling between two pieces of suture. Other embodiments may include terminal ends of two suture lengths whereby each length includes a knot included within the conduit. Other embodiments may include conduits that couple two suture lengths together. In such a case the suture lengths may or may not directly contact each other. Other embodiments may include a conduit that includes a knot in a monolithic suture length that traverses the conduit. Other embodiments may include a conduit immediately adjacent a knot in a monolithic suture length that traverses the conduit.

Figure 16:
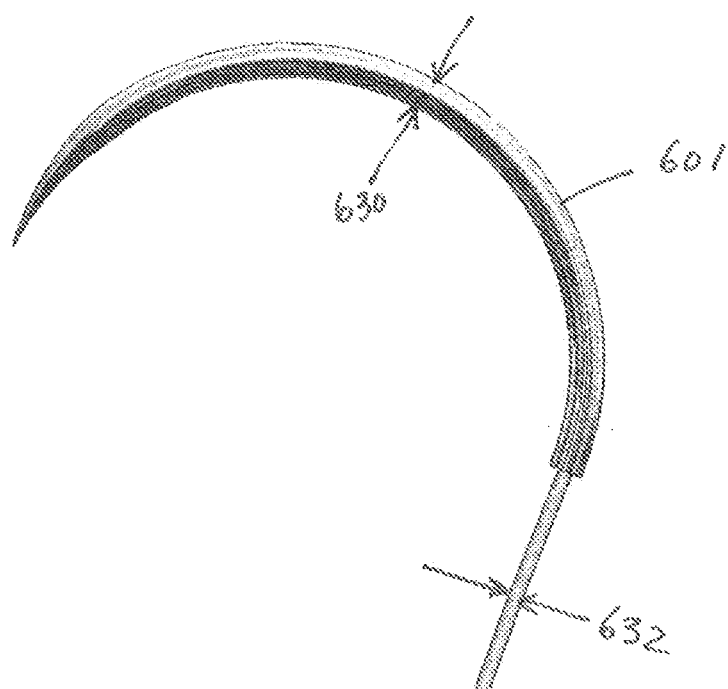
FIG. 16 includes an embodiment of a needle.

FIG. 16 includes a first needle 601 that has a first maximum outer diameter 630; the first distal conduit has a second maximum outer diameter (see diameter 531 of FIG. 15); and the first chord has third maximum outer diameter 632 that is less than (a) the first maximum outer diameter, and (b) the second maximum outer diameter.

Figure 2:
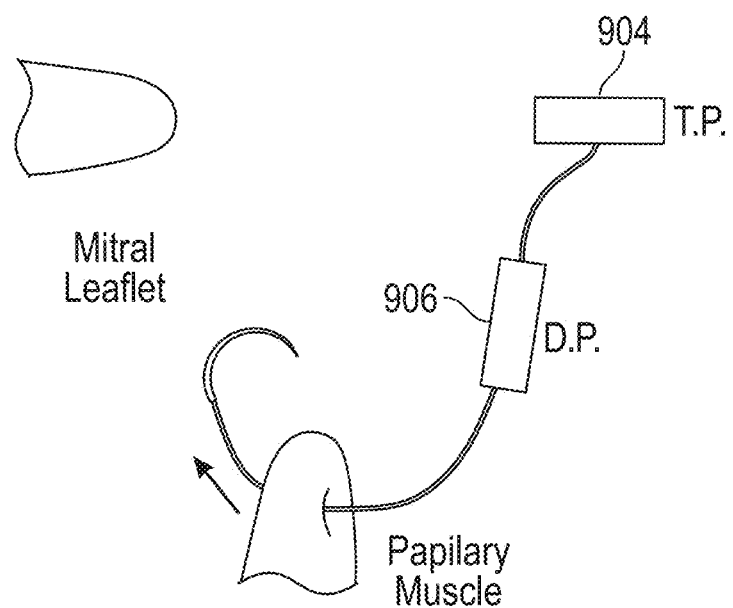
FIGS. 2, 3, 4, 5, 6, 7 depict an embodiment of a method of deploying a chordae tendineae system.
Figures 3, 4:
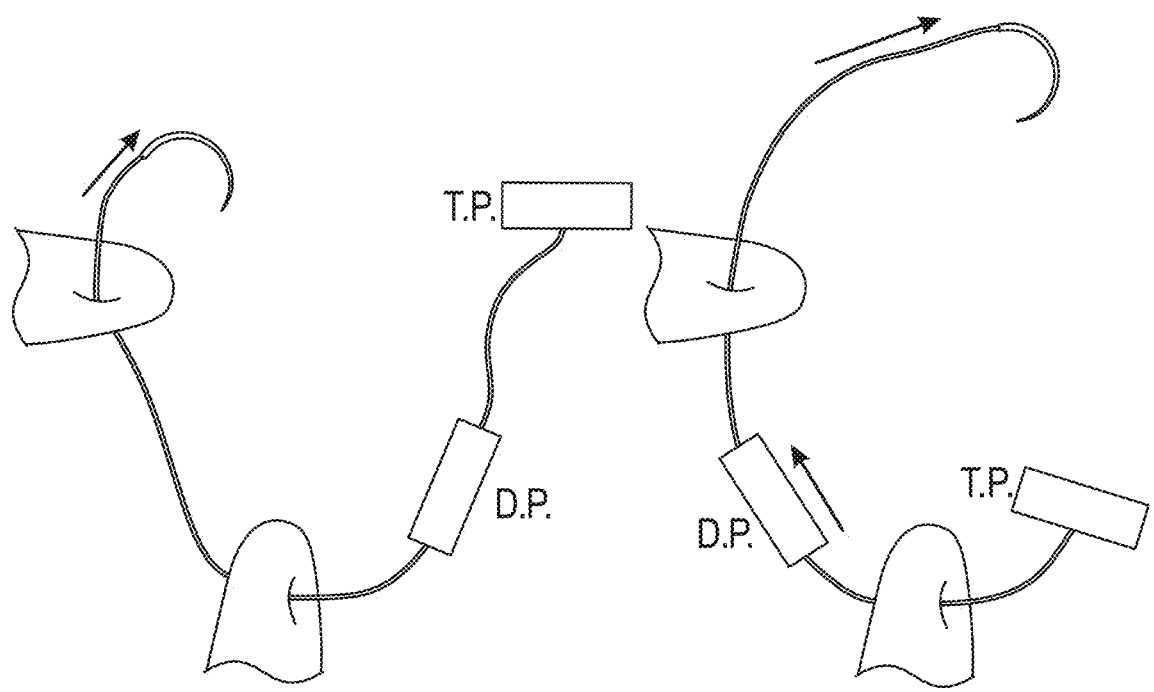
Figures 5, 6:
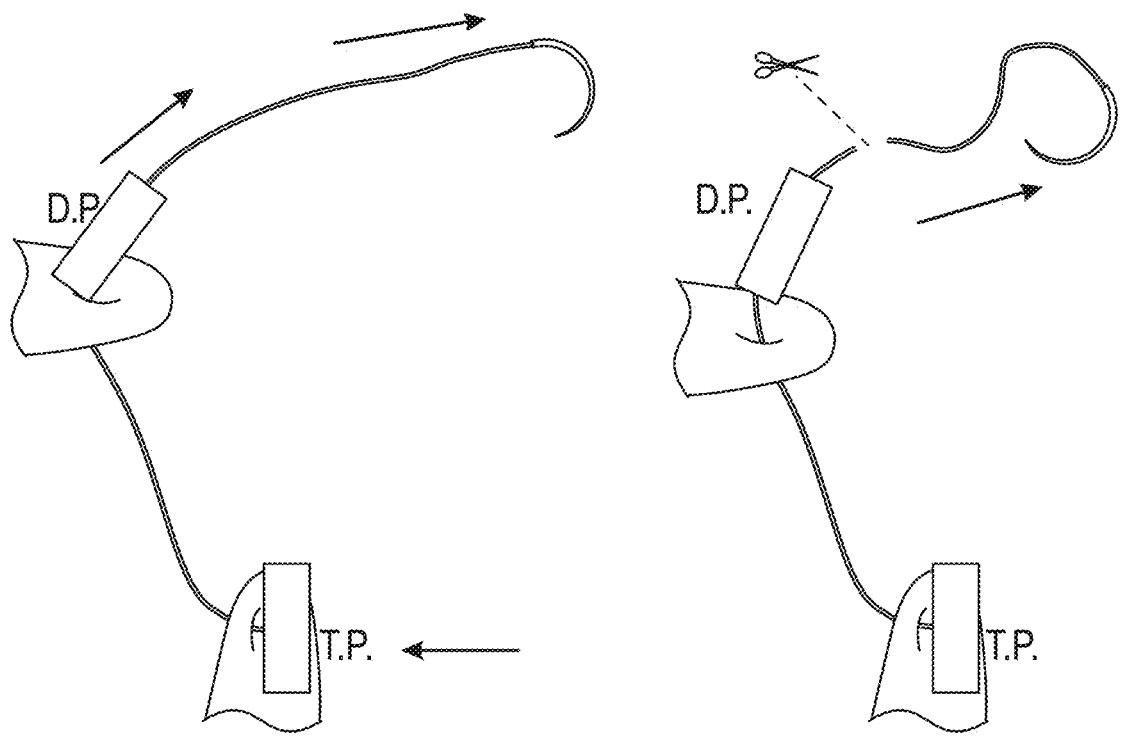
Figure 7:
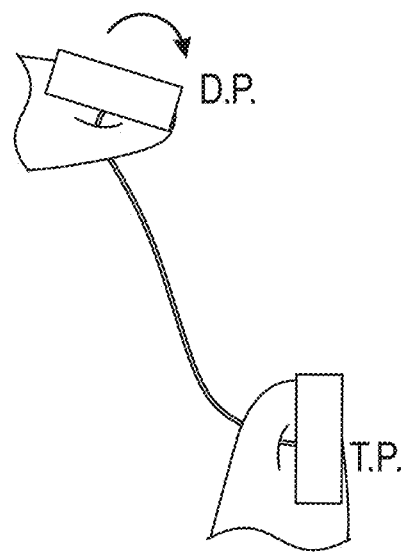
Figure 17:
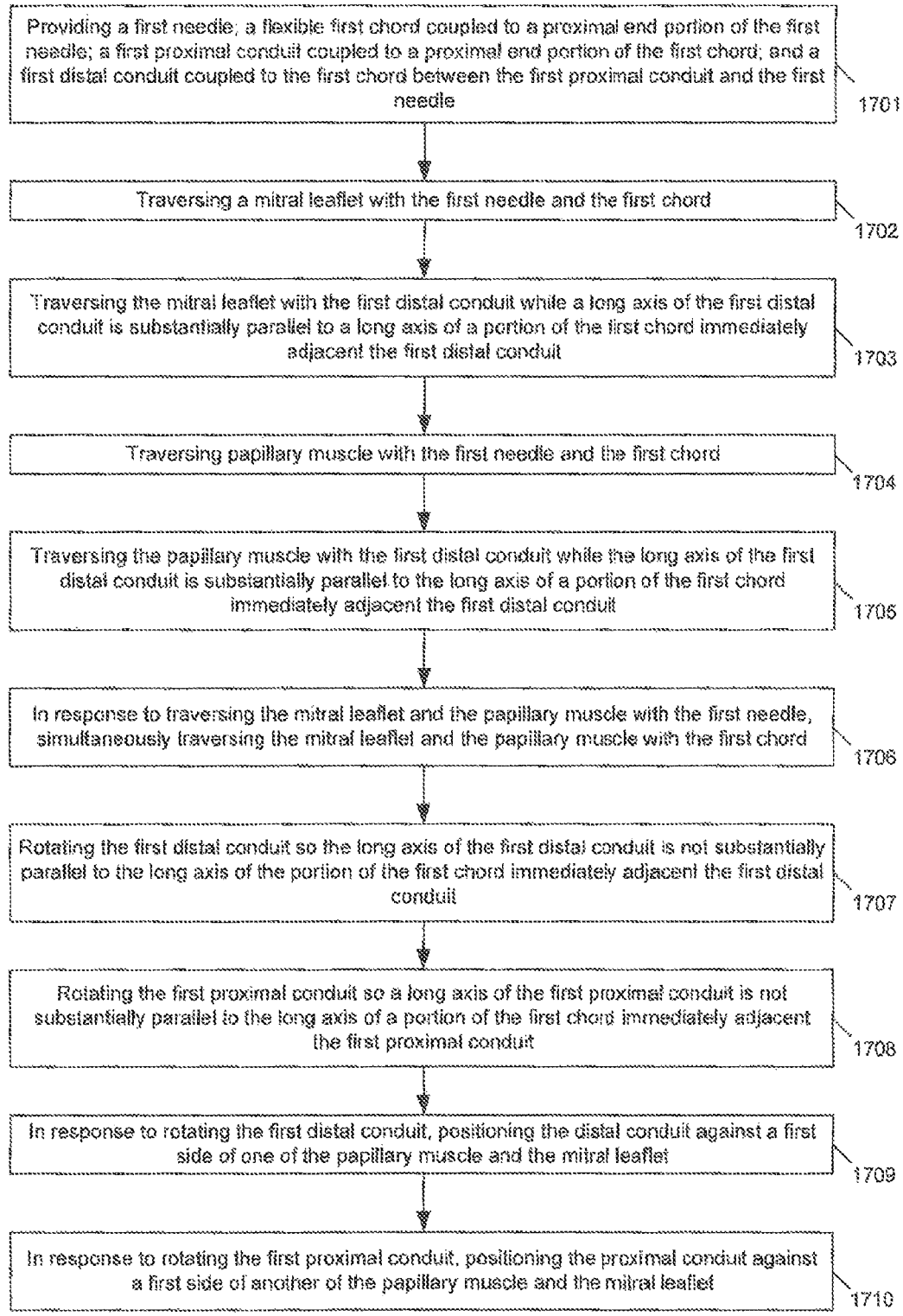
FIG. 17 includes an embodiment of a method of deploying a chordae tendineae system.

FIG. 17 includes a method 1700. Block 1701 includes providing a first needle; a flexible first chord coupled to a proximal end portion of the first needle; a first proximal conduit coupled to a proximal end portion of the first chord; a first distal conduit coupled to the first chord between the first proximal conduit and the first needle. Block 1702 includes traversing a mitral leaflet with the first needle and the first chord (FIG. 3). Block 1703 includes traversing the mitral leaflet with the first distal conduit while a long axis of the first distal conduit is substantially parallel to a long axis of a portion of the first chord immediately adjacent the first distal conduit (FIG. 5). Block 1704 includes traversing papillary muscle with the first needle and the first chord (FIG. 2). Block 1705 includes traversing the papillary muscle with the first distal conduit while the long axis of the first distal conduit is substantially parallel to the long axis of a portion of the first chord immediately adjacent the first distal conduit (FIG. 4). Block 1706 includes in response to traversing the mitral leaflet and the papillary muscle with the first needle, simultaneously traversing the mitral leaflet and the papillary muscle with the first chord (FIG. 6). Block 1707 includes rotating the first distal conduit so the long axis of the first distal conduit is not substantially parallel to the long axis of the portion of the first chord immediately adjacent the first distal conduit (FIG. 7). Block 1708 includes rotating the first proximal conduit so a long axis of the first proximal conduit is not substantially parallel to the long axis of a portion of the first chord immediately adjacent the first proximal conduit. Block 1709 includes in response to rotating the first distal conduit, positioning the distal conduit against a first side of one of the papillary muscle and the mitral leaflet (FIG. 7). Block 1710 includes in response to rotating the first proximal conduit, positioning the proximal conduit against a first side of another of the papillary muscle and the mitral leaflet (FIG. 7).

FIGS. 2, 3, 4, 5, 6, 7 illustrate initial penetration of the papillary muscle and then the leaflet but other embodiments reverse the process. These figures also show versions of pledgets that could be PTFE discs, conduits (e.g., FIG. 15), and the like. In other words, the block pledgets of FIG. 2 are somewhat generic and can include, for example, the embodiments of FIGS. 18(A)-18(E). FIGS. 11(A), 11(B), 11(C), 11(D) show a method of deployment with a PTFE proximal disc 704 and distal conduit 706 being deployed to papillary muscle and then a leaflet but other embodiments occur in reverse order (i.e., through the mitral valve and then papillary muscle or other tissue the physician desires to anchor the cord to).

Example 1 includes an artificial chordae tendineae system comprising: a first needle; a flexible first chord coupled to a proximal end portion of the first needle; a first proximal conduit coupled to a proximal end portion of the first chord; a first distal conduit coupled to the first chord between the first proximal conduit and the first needle; wherein the first chord includes a long axis when the first chord is fully extended into a linear orientation, the first proximal conduit includes a long axis, and the first distal conduit includes a long axis; wherein the long axes of the first proximal and distal conduits are substantially parallel to the long axis of the first chord in a first system orientation; wherein the first proximal and distal conduits are each configured to rotate when permanently deployed into a patient in a second system orientation such that the long axes of the first proximal and distal conduits are not parallel to the long axis of the first chord.

Thus, some embodiments include at least two pledgets. Those pledgets may include conduits such as element 506 of FIG. 15. Two conduit pledgets may be advantageous when, for example, both pledgets will be advanced through tissue. For example, in the embodiment of FIG. 9 element 406 may be advanced through a leaflet and element 404 may be advanced through papillary tissue. However, while FIG. 9 shows a needle for each of the conduits some embodiments are not so limited and may only include a single needle. In such a case (e.g., FIG. 1 where elements 206 and 204 are both conduits) only one of the conduits may be advanced through tissue (e.g., leaflet and papillary muscle) while the other conduit merely is placed against tissue without advancing through it.

Conduits, such as those of FIG. 15, FIG. 18(E), and FIG. 12 have advantages when it comes to advancing through tissue. For example, the axis of the conduit and chord may be advanced through tissue when oriented in a low resistance profile, such as FIG. 18(G) or FIG. 19(A). However, the conduit may then rotate into a high resistance profile when permanently implanted and placed adjacent tissue, such as FIG. 18(H) or FIG. 19(B).

Example 2 includes the system of example 1 comprising: a second needle; a flexible second chord coupled to a proximal end portion of the second needle; a second proximal conduit coupled to a proximal end portion of the second chord; a second distal conduit coupled to the second chord between the second proximal conduit and the second needle; wherein the second chord includes a long axis when the second chord is fully extended into a linear orientation, the second proximal conduit includes a long axis, and the second distal conduit includes a long axis; wherein the long axes of the second proximal and distal conduits are substantially parallel to the long axis of the second chord in an additional first system orientation; wherein the second proximal and distal conduits are each configured to rotate when permanently deployed into a patient in an additional second system orientation such that the long axes of the second proximal and distal conduits are not parallel to the long axis of the second chord; wherein the first chord has a first length between its first proximal and distal conduits and the second chord has a second length between its second proximal and distal conduits substantially equal to the first length.

Thus, a kit may include multiple structures such as system 200 of FIG. 1. The structures may each have the same chord length.

Example 3 includes the system of example 1 comprising: a second needle; a flexible second chord coupled to a proximal end portion of the second needle; a second proximal conduit coupled to a proximal end portion of the second chord; a second distal conduit coupled to the second chord between the second proximal conduit and the second needle; wherein the second chord includes a long axis when the second chord is fully extended into a linear orientation, the second proximal conduit includes a long axis, and the second distal conduit includes a long axis; wherein the long axes of the second proximal and distal conduits are substantially parallel to the long axis of the second chord in an additional first system orientation; wherein the second proximal and distal conduits are each configured to rotate when permanently deployed into a patient in an additional second system orientation such that the long axes of the second proximal and distal conduits are not parallel to the long axis of the second chord; wherein the first chord has a first length between its first proximal and distal conduits and the second chord has a second length between its second proximal and distal conduits that is unequal to the first length.

Thus, a kit may include multiple structures such as system 200 of FIG. 1. The structures may each have a different chord length.

Example 4 includes the system of example 1, comprising: a first proximal obstruction between the first proximal conduit and a proximal end of the first chord; and a first distal obstruction between the first distal conduit and the first needle; a second distal obstruction between the first proximal and distal conduits; wherein each of the first proximal obstruction, the first distal obstruction, and the second distal obstruction includes an outer diameter greater than an outer diameter of the first chord.

For example, FIG. 12 shows how knots 818, 813 can keep conduit 806 from sliding along chord 802. Such "bracketing" knots can be used for proximal conduits (e.g., conduit 404 of FIG. 9) as well.

Example 5 includes the system of example 1, wherein the first chord is monolithic and passes through the first distal conduit.

Example 6 includes the system of example 1, wherein the first chord is monolithic and passes through the first proximal and distal conduits.

For example, chord 202 (FIG. 1) may be monolithic and constitute a single piece of suture (all formed from one source without joining several pieces together with knots, welds, our couplers) that extends from needle 201 to pledget 204.

Example 7 includes the system of example 1, wherein portions of the first proximal and distal conduits are substantially statically coupled to the first chord so the portions of the first proximal and distal conduits do not slide along the first chord by more than 1 mm.

For example, FIG. 12 shows how knots 818, 813 can keep conduit 806 from sliding along chord 802. Such "bracketing" knots can be used for proximal conduits (e.g., conduit 404 of FIG. 9) as well.

Example 8 includes the system of example 1, wherein the first distal conduit is deformable.

This may be particularly useful when the distal conduit is likely to be the pledget that advances through tissue. For example, in FIG. 2-6 the distal pledget 906 is advanced through tissue twice whereas proximal pledget 904 is not advanced through tissue. In such a case pledget 906 may be made deformable (e.g., Nitinol) whereas pledget 904 is not necessarily made deformable.

Example 9 includes the system of example 1, wherein the first chord includes a first chord material, the first proximal conduit includes a first proximal conduit material, and the first distal conduit includes a first distal conduit material that is the same as the first chord material and the first proximal conduit material.

Example 10 includes the system of example 9, wherein the first distal conduit material includes at least one of polytetrafluoroethylene and expanded polytetrafluoroethylene.

Example 11 includes the system of example 1 comprising: a second needle; a flexible second chord coupled to a proximal end portion of the second needle, the first proximal conduit being coupled to a proximal end portion of the second chord; a second distal conduit coupled to the second chord between the first proximal conduit and the second needle; wherein the second chord includes a long axis when the second chord is fully extended into a linear orientation, and the second distal conduit includes a long axis; wherein the long axis of the second distal conduit is substantially parallel to the long axis of the second chord in an additional first system orientation; wherein the second distal conduit is configured to rotate when permanently deployed into the patient in an additional second system orientation such that the long axis of the second distal conduit is not parallel to the long axis of the second chord.

For example, with FIG. 10 proximal pledget 304 may be advanced through papillary tissue while the other "arms" are each advanced through leaflet tissue, all using minimal profiles for advancing through tissue (e.g., FIG. 18(G)) and obstructing profiles for permanent implantation (e.g., FIG. 18(H)).

For example, with FIG. 8 distal pledgets 1006, 1006' may be advanced through papillary and leaflet tissue while proximal pledget 1004 is located adjacent papillary tissue. The distal pledgets may include minimal profiles for advancing through tissue (e.g., FIG. 18(G)) and obstructing profiles for permanent implantation (e.g., FIG. 18(H)). However, pledgets 1006, 1006' are not limited to conduit embodiments and pledgets may use other embodiments (e.g., FIG. 18(A)) described or relied upon herein.

Example 12 includes the system of example 11 comprising: a third needle; a flexible third chord coupled to an end portion of the third needle and to the first proximal conduit; wherein the third chord is between the first proximal conduit and the third needle.

For example, the needle 301" of FIG. 10 helps advance pledget 304 through papillary tissue.

Example 13 includes the system of example 1 comprising: a second needle; a flexible second chord coupled to an end portion of the second needle and to the first proximal conduit; wherein the second chord is between the first proximal conduit and the second needle.

For example, the needle 401' of FIG. 9 helps advance pledget 404 through papillary tissue.

Example 14 includes the system of example 1, wherein: the first distal conduit includes first and second faces; one of the first and second faces includes a first aperture; a sidewall of the first conduit, located between the first and second faces, includes a sidewall aperture that does not directly connect to the first aperture; the sidewall aperture is configured to include a portion of the first chord when the system is in the second system orientation but not when the system is in the first system orientation.

For example, see FIG. 15.

Example 15 includes the system of example 1, wherein the first distal conduit has a beveled edge to facilitate traversal of the first distal conduit through tissue.

For example, see FIG. 15.

Example 16 includes the system of example 1, wherein: the first needle has a first maximum outer diameter; the first distal conduit has a second maximum outer diameter; and the first chord has third maximum outer diameter that is less than (a) the first maximum outer diameter, and (b) the second maximum outer diameter.

For example, see FIG. 16.

Example 17 includes a method comprising providing a first needle; a flexible first chord coupled to a proximal end portion of the first needle; a first proximal conduit coupled to a proximal end portion of the first chord; a first distal conduit coupled to the first chord between the first proximal conduit and the first needle; traversing a mitral leaflet with the first needle and the first chord; traversing the mitral leaflet with the first distal conduit while a long axis of the first distal conduit is substantially parallel to a long axis of a portion of the first chord immediately adjacent the first distal conduit; traversing papillary muscle with the first needle and the first chord; traversing the papillary muscle with the first distal conduit while the long axis of the first distal conduit is substantially parallel to the long axis of a portion of the first chord immediately adjacent the first distal conduit; in response to traversing the mitral leaflet and the papillary muscle with the first needle, simultaneously traversing the mitral leaflet and the papillary muscle with the first chord; rotating the first distal conduit so the long axis of the first distal conduit is not substantially parallel to the long axis of the portion of the first chord immediately adjacent the first distal conduit; rotating the first proximal conduit so a long axis of the first proximal conduit is not substantially parallel to the long axis of a portion of the first chord immediately adjacent the first proximal conduit; in response to rotating the first distal conduit, positioning the distal conduit against a first side of one of the papillary muscle and the mitral leaflet; in response to rotating the first proximal conduit, positioning the proximal conduit against a first side of another of the papillary muscle and the mitral leaflet.

Figure 13:
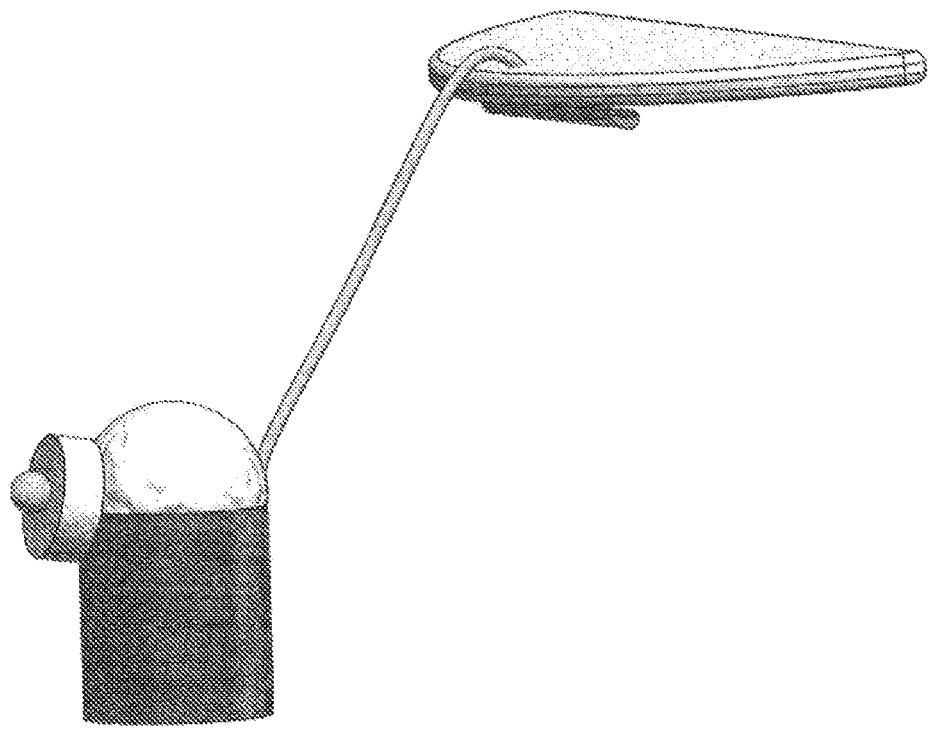
FIGS. 13 and 14 show different deployment orientations for an embodiment.

Numerous examples of implantation techniques are provided herein. For example, FIGS. 2-6 illustrate advancing a single pledget through tissue twice. The pledget may be ePTFE, felt, conduits (e.g., FIG. 15), and the like. The traversal may begin with papillary muscle and end with the leaflet. However, the process may be reversed and begin with leaflet tissue and end with papillary muscle. FIGS. 11(A)-11(D) show a process similar to FIGS. 2-6 but explicitly include two types of pledgets: a deployable or lead pledget 706 (which may be a low profile conduit such as FIG. 15) and a terminal or obstructing profile pledget 704 (which is not a conduit like the embodiment of FIG. 15) that is not necessarily meant to be advanced through tissue. FIGS. 13 and 14 illustrate how a deployable pledget (e.g., FIG. 15) may be permanently coupled to leaflet tissue (e.g., FIG. 13) or papillary tissue (e.g., FIG. 14).

Example 18 includes the method comprising traversing the mitral leaflet with the first needle and the first chord after traversing the papillary muscle with the first needle and the first chord.

Example 19 includes an artificial chordae tendineae system comprising: a first needle; a flexible first chord coupled to a proximal end portion of the first needle; a first proximal pledget coupled to a proximal end portion of the first chord; a first distal conduit coupled to the first chord between the first proximal pledget and the first needle; wherein the first chord includes a long axis when the first chord is fully extended into a linear orientation, and the first distal conduit includes a long axis; wherein the long axis of the first distal conduit is substantially parallel to the long axis of the first chord in a first system orientation; wherein the distal conduit is configured to rotate when permanently deployed into a patient in a second system orientation such that the long axis of the distal conduit is not parallel to the long axis of the first chord.

Figure 11A:
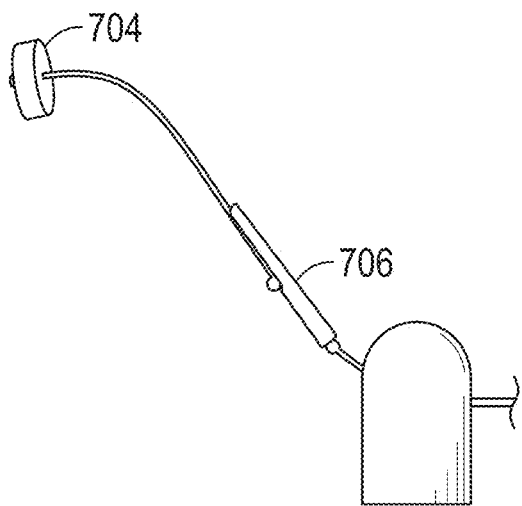
FIGS. 11(A), 11(B), 11(C), and 11(D) depict an embodiment of a method of deploying a chordae tendineae system.
Figure 11B:
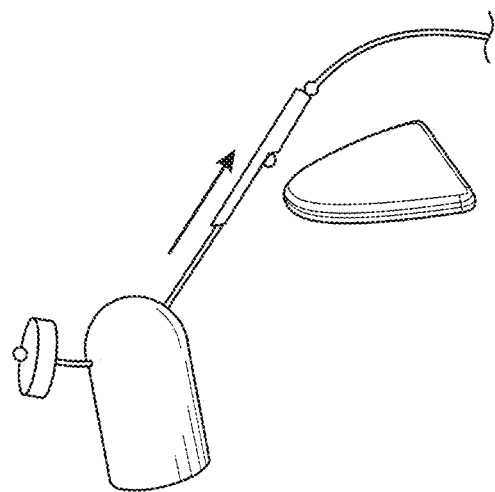
Figure 11C:
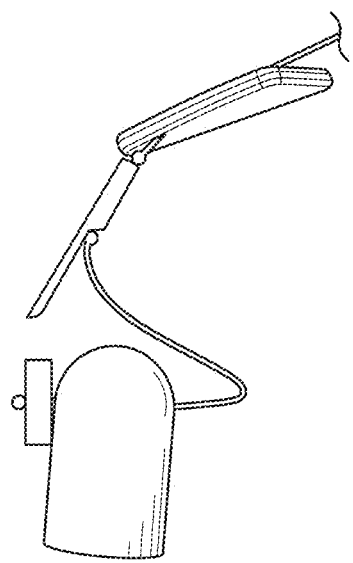
Figure 11D:
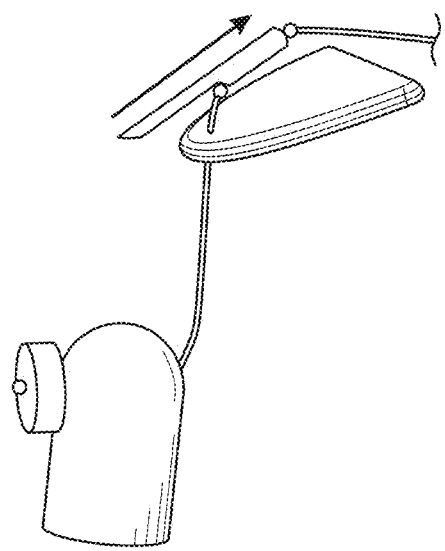

For example, FIGS. 11(A)-11(D) and 12-14 illustrate embodiments with a proximal pledget (e.g., element 704 of FIG. 11(A)) that does not necessarily include a conduit and a distal conduit (e.g., element 706 of FIG. 11(A)). Such an embodiment may be particularly useful for situations where the deployable pledget (e.g., element 706 of FIG. 11(A)) will advance through tissue but the proximal pledget (e.g., element 704 of FIG. 11(A)) does not advance through tissue.

Example 20 includes the system of example 19 comprising: a second needle; a flexible second chord coupled to a proximal end portion of the second needle; a second proximal pledget coupled to a proximal end portion of the second chord; a second distal conduit coupled to the second chord between the second proximal pledget and the second needle; wherein the second chord includes a long axis when the second chord is fully extended into a linear orientation, and the second distal conduit includes a long axis; wherein the long axis of the second distal conduit is substantially parallel to the long axis of the second chord in an additional first system orientation; wherein the second distal conduit is configured to rotate when permanently deployed into a patient in an additional second system orientation such that the long axis of the second distal conduit is not parallel to the long axis of the second chord; wherein the first chord has a first length between its first proximal pledget and first distal conduit and the second chord has a second length between its second proximal pledget and second distal conduit substantially equal to the first length.

Example 21 includes the system of example 19 comprising: a second needle; a flexible second chord coupled to a proximal end portion of the second needle; a second proximal pledget coupled to a proximal end portion of the second chord; a second distal conduit coupled to the second chord between the second proximal pledget and the second needle; wherein the second chord includes a long axis when the second chord is fully extended into a linear orientation, and the second distal conduit includes a long axis; wherein the long axis of the second distal conduit is substantially parallel to the long axis of the second chord in an additional first system orientation; wherein the second distal conduit is configured to rotate when permanently deployed into a patient in an additional second system orientation such that the long axis of the second distal conduit is not parallel to the long axis of the second chord; wherein the first chord has a first length between its first proximal pledget and first distal conduit and the second chord has a second length between its second proximal pledget and second distal conduit that is unequal to the first length.

Example 22 includes the system of example 19, comprising: a first distal obstruction between the first distal conduit and the first needle; a second distal obstruction between the first proximal pledget and first distal conduit; wherein each of the first distal obstruction and the second distal obstruction includes an outer diameter greater than an outer diameter of the first chord.

Example 23 includes the system of example 19, wherein the first chord is monolithic and passes through the first distal conduit.

Example 24 includes the system of example 19, wherein the first chord is monolithic and passes through the first proximal pledget and the first distal conduit.

Example 25 includes the system of example 19, wherein a portion of the first distal conduit is substantially statically coupled to the first chord so the portion of the first distal conduit does not slide along the first chord by more than 1 mm.

Example 26 includes the system of example 19, wherein the first distal conduit is deformable.

Example 27 includes the system of example 19, wherein the first chord includes a first chord material, the first proximal pledget includes a first proximal pledget material, and the first distal conduit includes a first distal conduit material that is the same as the first chord material and the first proximal pledget material.

Example 28 includes the system of example 27, wherein the first distal conduit material includes at least one of polytetrafluoroethylene and expanded polytetrafluoroethylene.

Example 29 includes the system of example 19 comprising: a second needle; a flexible second chord coupled to a proximal end portion of the second needle, the first proximal pledget being coupled to a proximal end portion of the second chord; a second distal conduit coupled to the second chord between the first proximal pledget and the second needle; wherein the second chord includes a long axis when the second chord is fully extended into a linear orientation, and the second distal conduit includes a long axis; wherein the long axis of the second distal conduit is substantially parallel to the long axis of the second chord in an additional first system orientation; wherein the second distal conduit is configured to rotate when permanently deployed into the patient in an additional second system orientation such that the long axis of the second distal conduit is not parallel to the long axis of the second.

Example 30 includes the system of example 29 comprising: a third needle; a flexible third chord coupled to an end portion of the third needle and to the first proximal pledget; wherein the third chord is between the first proximal pledget and the third needle.

Example 31 includes the system of example 19 comprising: a second needle; a flexible second chord coupled to an end portion of the second needle and to the first proximal pledget; wherein the second chord is between the first proximal pledget and the second needle.

Example 32 includes the system of example 19, wherein: the first distal conduit includes first and second faces; one of the first and second faces includes a first aperture; a sidewall of the first conduit, located between the first and second faces, includes a sidewall aperture that does not directly connect to the first aperture; the sidewall aperture is configured to include a portion of the first chord when the system is in the second system orientation but not when the system is in the first system orientation.

Example 33 includes the system of example 19, wherein the first distal conduit has a beveled edge to facilitate traversal of the first distal conduit through tissue.

Example 34 includes the system of example 19, wherein: the first needle has a first maximum outer diameter; the first distal conduit has a second maximum outer diameter; and the first chord has third maximum outer diameter that is less than (a) the first maximum outer diameter, and (b) the second maximum outer diameter.

Example 35 includes an artificial chordae tendineae system comprising: a first needle; a flexible first chord coupled to a proximal end portion of the first needle; a first proximal pledget coupled to a proximal end portion of the first chord; a first distal pledget coupled to the first chord between the first proximal pledget and the first needle.

For example, FIG. 18(B) or 18(F) (which no longer show a needle that was coupled to element 101) has two pledgets, neither of which are necessarily conduits. FIG. 2 includes two symbolic pledgets 204, 206, either or both of which may take on forms shown in any of FIGS. 18(A)-18(F) or elsewhere herein.

Example 36 includes the system of example 35 comprising: a second needle; a flexible second chord coupled to a proximal end portion of the second needle; a second proximal pledget coupled to a proximal end portion of the second chord; a second distal pledget coupled to the second chord between the second proximal pledget and the second needle; wherein first chord has a first length between its first proximal pledget and first distal pledget and the second chord has a second length between its second proximal pledget and second distal pledget substantially equal to the first length.

Example 37 includes the system of example 35 comprising: a second needle; a flexible second chord coupled to a proximal end portion of the second needle; a second proximal pledget coupled to a proximal end portion of the second chord; a second distal pledget coupled to the second chord between the second proximal pledget and the second needle; wherein first chord has a first length between its first proximal pledget and first distal pledget and the second chord has a second length between its second proximal pledget and second distal pledget that is unequal to the first length.

Example 38 includes the system of example 35, wherein the first chord is monolithic and passes through the first distal pledget.

Example 39 includes the system of example 35, wherein the first chord is monolithic and passes through the first proximal pledget and the first distal pledget.

Example 40 includes the system of example 35, wherein the first distal pledget is deformable.

Example 41 includes the system of example 35, wherein the first chord includes a first chord material, the first proximal pledget includes a first proximal pledget material, and the first distal pledget includes a first distal pledget material that is the same as the first chord material and the first proximal pledget material.

Example 42 includes the system of example 41, wherein the first distal pledget material includes at least one of polytetrafluoroethylene and expanded polytetrafluoroethylene.

Example 43 includes the system of example 35 comprising: a second needle; a flexible second chord coupled to a proximal end portion of the second needle, the first proximal pledget being coupled to a proximal end portion of the second chord; a second distal pledget coupled to the second chord between the first proximal pledget and the second needle.

Example 44 includes the system of example 43 comprising: a third needle; a flexible third chord coupled to an end portion of the third needle and to the first proximal pledget; wherein the third chord is between the first proximal pledget and the third needle.

Example 45 includes the system of example 35 comprising: a second needle; a flexible second chord coupled to an end portion of the second needle and to the first proximal pledget; wherein the second chord is between the first proximal pledget and the second needle.

Example 46 includes the system of example 35, wherein: the first needle has a first maximum outer diameter; the first distal pledget has a second maximum outer diameter; and the first chord has third maximum outer diameter that is less than (a) the first maximum outer diameter, and (b) the second maximum outer diameter.

Example 47 includes an artificial chordae tendineae system comprising: a first needle; a flexible first chord coupled to a proximal end portion of the first needle; a first proximal pledget coupled to a proximal end portion of the first chord; a first distal conduit coupled to the first chord between the first proximal pledget and the first needle; wherein: the first distal conduit includes first and second faces; one of the first and second faces includes a first aperture; a sidewall of the first conduit, located between the first and second faces, includes a sidewall aperture that does not directly connect to the first aperture; the sidewall aperture is configured to include a portion of the first chord when the first distal conduit is permanently implanted adjacent tissue but not when the first distal conduit is traversing the tissue before being permanently implanted adjacent the tissue.

For example, FIGS. 11(A)-11(D) and 12-14 illustrate embodiments with a proximal pledget (e.g., element 704 of FIG. 11(A)) that does not necessarily include a conduit and a distal conduit (e.g., element 706 of FIG. 11(A) or FIG. 15). Such an embodiment may be particularly useful for situations where the deployable pledget (e.g., element 706 of FIG. 11(A)) will advance through tissue but the proximal pledget (e.g., element 704 of FIG. 11(A)) does not advance through tissue. See also FIGS. 18(G) and 18(H) regarding a sidewall aperture including suture (FIG. 18(H)) and the sidewall aperture not including suture (FIG. 18(G)).

Example 48 includes the system of example 47, wherein the first chord is monolithic and passes through the first distal conduit.

Example 49 includes the system of example 47, wherein the first distal conduit has a beveled edge to facilitate traversal of the first distal conduit through the tissue.

For example, a single chord 802 passes.

Example 50 includes the system of example 47, wherein: the first needle has a first maximum outer diameter; the first distal conduit has a second maximum outer diameter; and the first chord has third maximum outer diameter that is less than (a) the first maximum outer diameter, and (b) the second maximum outer diameter.

Example 51 includes the system of example 1, wherein: the first distal conduit includes first and second end portions; the first end portion includes a first face comprising a first aperture that includes the first chord; the second end portion is configured to directly contact the first chord when the system is in the first system orientation but to not directly contact the first chord when the system is in the second system orientation.

The foregoing description of the embodiments of the invention has been presented for the purposes of illustration and description. It is not intended to be exhaustive or to limit the invention to the precise forms disclosed. This description and the claims following include terms, such as left, right, top, bottom, over, under, upper, lower, first, second, etc. that are used for descriptive purposes only and are not to be construed as limiting. For example, terms designating relative vertical position refer to a situation where a side of a substrate is the "top" surface of that substrate; the substrate may actually be in any orientation so that a "top" side of a substrate may be lower than the "bottom" side in a standard terrestrial frame of reference and still fall within the meaning of the term "top." The embodiments of a device or article described herein can be manufactured, used, or shipped in a number of positions and orientations. Persons skilled in the relevant art can appreciate that many modifications and variations are possible in light of the above teaching. Persons skilled in the art will recognize various equivalent combinations and substitutions for various components shown in the Figures. It is therefore intended that the scope of the invention be limited not by this detailed description, but rather by the claims appended hereto.

The invention claimed is:

1. An artificial chordae tendineae system comprising:
   a knot;
   a first subassembly including: (a) a first needle; (b) a flexible first chord coupled to the first needle and the knot; and (c) a first conduit coupled to the first chord and located between the knot and the first needle;
   a second subassembly including: (a) a second needle; (b) a flexible second chord coupled to the second needle and the knot; and (c) a second conduit coupled to the second chord and located between the knot and the second needle;
   a third subassembly including: (a) a third needle; (b) a flexible third chord coupled to the third needle and the knot; and (c) a third conduit coupled to the third chord and located between the knot and the third needle;
   wherein: (a) when the first chord is fully extended along a long axis of the first chord the first conduit is a first distance from the knot; (b) when the second chord is fully extended along a long axis of the second chord the second conduit is a second distance from the knot; (c) when the third chord is fully extended along a long axis of the third chord the third conduit is a third distance from the knot, and (d) the first distance is unequal to the second distance and the first distance is unequal to the third distance;
   wherein: (a) a long axis of the first conduit is substantially parallel to the long axis of the first chord in a first system orientation; and (b) the first conduit is configured to rotate when permanently deployed into a patient in a second system orientation such that the long axis of the first conduit is not parallel to the long axis of the first chord.

2. The system of claim 1 comprising:
   a first obstruction between the first conduit and the first needle;
   a second obstruction between the second conduit and the second needle;
   wherein each of the first obstruction and the second obstruction includes an outer diameter greater than an outer diameter of the first chord.

3. The system of claim 1, wherein the first distance is less than the second distance and the first distance is less than the third distance.

4. The system of claim 1, wherein the first chord is monolithic and passes through the first conduit.

5. The system of claim 1 wherein the first chord is monolithic and passes through the first conduit and the second conduit.

6. The system of claim 1, wherein a portion of the first conduit is substantially statically coupled to the first chord so the portion of the first conduit does not slide along the first chord by more than 1 mm.

7. The system of claim 1 wherein the first chord includes a first chord material, the first conduit includes a first conduit material, and the second conduit includes a second conduit material that is the same as the first chord material and the first conduit material.

8. The system of claim 1, wherein:
   the first conduit includes first and second end portions;
   the first end portion includes a first face comprising a first aperture that includes the first chord;
   the second end portion is configured to directly contact the first chord when the system is in the first system orientation but to not directly contact the first chord when the system is in the second system orientation.

9. The system of claim 1, wherein:
   the first conduit includes first and second faces;
   one of the first and second faces includes a first aperture;
   a sidewall of the first conduit, located between the first and second faces, includes a sidewall aperture that does not directly connect to the first aperture;
   the sidewall aperture is configured to include a portion of the first chord when the system is in the second system orientation but not when the system is in the first system orientation.

10. The system of claim 1, wherein the first distal conduit has a beveled edge to facilitate traversal of the first distal conduit through tissue.

11. The system of claim 1, wherein:
    the first needle has a first maximum outer diameter;
    the first distal conduit has a second maximum outer diameter; and
    the first chord has a third maximum outer diameter that is less than (a) the first maximum outer diameter, and (b) the second maximum outer diameter.

12. The system of claim 1, wherein each of the first, second, and third chords couple to one another via the knot.

13. The system of claim 2, wherein the first obstruction includes a first additional knot and the second obstruction includes a second additional knot.

* * * * *